United States Patent
Cohen et al.

(10) Patent No.: US 11,739,296 B2
(45) Date of Patent: *Aug. 29, 2023

(54) METHODS AND MATERIALS FOR EXPANDING ANTIGEN-SPECIFIC T CELLS IN CULTURE

(71) Applicants: Mayo Foundation for Medical Education and Research, Rochester, MN (US); University of Washington, Seattle, WA (US)

(72) Inventors: Peter A. Cohen, Scottsdale, AZ (US); Sandra J. Gendler, Scottsdale, AZ (US); Latha B. Pathangey, Scottsdale, AZ (US); Dustin B. McCurry, Phoenix, AZ (US); Jessica E. Gorman, Scottsdale, AZ (US); Mary L. Disis, Renton, WA (US)

(73) Assignees: Mayo Foundation for Medical Education and Research, Rochester, MN (US); University of Washington, Seattle, WA (US)

(*) Notice: Subject to any disclaimer, the term of this patent is extended or adjusted under 35 U.S.C. 154(b) by 740 days.

This patent is subject to a terminal disclaimer.

(21) Appl. No.: 16/848,110

(22) Filed: Apr. 14, 2020

(65) Prior Publication Data
US 2020/0248140 A1    Aug. 6, 2020

Related U.S. Application Data

(63) Continuation of application No. 15/754,216, filed as application No. PCT/US2016/046816 on Aug. 12, 2016, now Pat. No. 10,647,961.

(60) Provisional application No. 62/208,263, filed on Aug. 21, 2015.

(51) Int. Cl.
C12N 5/0783 (2010.01)
A61K 39/00 (2006.01)

(52) U.S. Cl.
CPC ........ *C12N 5/0636* (2013.01); *A61K 39/0011* (2013.01); *A61K 39/001106* (2018.08); *A61K 39/001153* (2018.08); *A61K 39/001156* (2018.08); *A61K 39/001168* (2018.08); *A61K 39/001169* (2018.08); *A61K 39/001188* (2018.08); *A61K 39/001191* (2018.08); *A61K 39/001192* (2018.08); *A61K 2039/5158* (2013.01); *C12N 2501/22* (2013.01); *C12N 2501/2307* (2013.01); *C12N 2501/51* (2013.01); *C12N 2501/515* (2013.01)

(58) Field of Classification Search
None
See application file for complete search history.

(56) References Cited

U.S. PATENT DOCUMENTS

| 7,977,095 B2 | 7/2011 | Bonyhadi et al. |
| 2010/0272700 A1 | 10/2010 | Cohen et al. |
| 2018/0245042 A1 | 8/2018 | Cohen et al. |

FOREIGN PATENT DOCUMENTS

| EP | 1956080 | 8/2008 |
| WO | WO 2001/62895 | 8/2001 |
| WO | WO 2011/146473 | 11/2011 |
| WO | WO 2014/039044 | 3/2014 |

OTHER PUBLICATIONS

Bonyhadi et al., "Expansion of Antigen-Specific CTL Using CD3/CD28 Paramagnetic Microbeads (Xcellate TM Beads). For Adoptive Cellular Therapy of Melanoma", Blood, 98(11):32B-33B, Nov. 2001.
Cohen et al. [Poster], "Culture conditions promoting innate immunity and homeostatic proliferation generate highly enriched, MUC1- or HER2/neu-specific CD4+ and CD8+ T cells (P4419)," J. Immunol,, 190(1 Suppl):205, May 1, 2013.
European Supplementary Search Report in European Application No. 16839809.7 dated Mar. 4, 2019, 85 pages.
Extended European Search Report in Europeam Application No. 16839809.7 dated May 21, 2019, 84 pages.
Jin et al., "Simplified method of the growth of human tumor infiltrating lymphocytes in gas-permeable flasks to numbers needed for patient treatment," J Immunother, 2012, 35(3): 283-292.
Knutson and Disis, "IL-12 enhances the generation of tumour antigen-specific Th1 CD4 T cells during ex vivo expansion," Clin Exp Immunol, Feb. 2004, 135: 322-329.
Pathangey et al., "Surrogate in vitro activation of innate immunity synergizes with interleukin-7 to unleash rapid antigen-driven outgrowth of CD4+ and CD8+ human peripheral blood T-cells naturally recognizing MUC1, HER2/neu and other tumor-associated antigens," Oncotarget, 8(7): 10785, Feb. 2017.
Paustian et al., "Extracellular ATP and Toll-like Receptor 2 Agonists Trigger in Human Monocytes an Activation Program that Favors T Helper 17," PLOS One, Jan. 2013, 8(1): 2.
PCT International Preliminary Report on Patentability in International Appln. No. PCT/US2016/46816, dated Feb. 28, 2018, 22 pages.

(Continued)

*Primary Examiner* — Daniel C Gamett
(74) *Attorney, Agent, or Firm* — Fish & Richardson P.C.

(57) ABSTRACT

This document provides methods and materials for expanding antigen-specific T cells (e.g., antigen-specific CD4$^+$ T cells and/or antigen-specific CD8$^+$ T cells) in culture. For example, methods and materials for performing a polyclonal stimulation step for a particular duration (e.g., from about 1 hour to about 48 hours) to increase the expansion of T cells having a desired antigen specificity are provided.

19 Claims, 29 Drawing Sheets

(56) References Cited

OTHER PUBLICATIONS

PCT International Search Report and Written Opinion in International Appln. No. PCT/US2016/46816, dated Feb. 1, 2017, 33 pages.
Schwartzentruber et al., "Specific release of granulocyte-macrophage colony-stimulating factor, tumor necrosis factor-alpha, and IFN-gamma by human tumor-infiltrating lymphocytes after autologous tumor stimulation," J Immunol, May 1991, 146(10): 3674-3681.
ThermoFisher [online], Dynabeads® CD3/CD2 CTSTM, ThermoFisher.com, retrieved on Sep. 10, 2015, URL <http://www.thermofisher.com/us/en/home/references/protocols/proteinsexpressionisolationandanalysis/tcellactivationandexpansion/dynabeadsclinexvivocd3cd28.html>, 7 pages.
Topalian et al., "Mechanism-driven biomarkers to guide immune checkpoint blockade in cancer therapy," Nat Rev Cancer, May 2016, 16(5): 275-287.
Zhong et al., "Augmentation of autologous T cell reactivity with acute myeloid leukemia (AML) blasts by toll-like receptor (TLR) agonists," Cancer Immunol. Immunother,, 64(6):737-744, Mar. 2015.
Ackerman et al., "Early phagosomes in dendritic cells form a cellular compartment sufficient for cross presentation of exogenous antigens," Proc. Natl. Acad. Sci. USA, Oct. 28, 2003, 100(22):12889-12894.
Brahmer et al., "Safety and activity of anti-PD-L1 antibody in patients with advanced cancer," N. Engl. J. Medicine, Jun. 28, 2012, 366(26):2455-2465.
Brimnes et al., "Generation of autologous tumor-specific T cells for adoptive transfer based on vaccination, in vitro restimulation and CD3/CD28 dynabead-induced T cell expansion," Cancer Immunol. Immunotherapy, Aug. 2012, 61(8):1221-1231.
Büning et al., "Do CARs need a driver's license? Adoptive cell therapy with chimeric antigen receptor-redirected T cells has caused serious adverse events," Hum. Gene Therapy, Sep. 2010, 21(9):1039-1042.
Carpenito et al., "Control of large, established tumor xenografts with genetically retargeted human T cells containing CD28 and CD137 domains," Proc. Natl. Acad. Sci. USA, Mar. 3, 2009, 106(9):3360-3365.
Chen et al., "Alternative processing for MHC class I presentation by immature and CpG-activated dendritic cells," Eur. J. Immunology, Apr. 2004, 34(4):952-960.
Chen et al., "Endolysosomal processing of exogenous antigen into major histocompatibility complex class I-binding peptides," Scand. J. Immunology, Jun. 2004, 59(6):545-552.
Colpitts et al., "IL-7 receptor expression provides the potential for long-term survival of both CD62Lhigh central memory T cells and Th1 effector cells during Leishmania major infection," J. Immunology, May 1, 2009, 182(9):5702-5711.
Czerniecki et al., "Targeting HER-2/neu in early breast cancer development using dendritic cells with staged interleukin-12 burst secretion," Cancer Research, Feb. 15, 2007, 67(4):1842-1852.
Dadmarz et al., "CD4+ T lymphocytes infiltrating human breast cancer recognise autologous tumor in an MHC-class-II restricted fashion," Cancer Immunol. Immunotherapy, Jan. 1995, 40(1):1-9.
Dang et al., "Tumor antigen-specific T-cell expansion is greatly facilitated by in vivo priming," Clin. Cancer Research, Mar. 15, 2007, 13(6):1883-1891.
De Jong et al., "Presence of tumor-infiltrating lymphocytes is an independent prognostic factor in type I and II endometrial cancer," Gynecol. Oncology, Jul. 2009, 114(1):105-110.
Delamarre et al., "Presentation of exogenous antigens on major histocompatibility complex (MHC) class I and MHC class II molecules is differentially regulated during dendritic cell maturation," J. Exp. Medicine, Jul. 7, 2003, 198(1):111-122.
Disis et al., "HER-2/neu vaccine-primed autologous T-cell infusions for the treatment of advanced stage HER-2/neu expressing cancers," Cancer Immunol. Immunotherapy, Feb. 2014, 63(2):101-109.
Dudley et al., "Adoptive cell transfer therapy following non-myeloablative but lymphodepleting chemotherapy for the treatment of patients with refractory metastatic melanoma," J. Clin. Oncology, Apr. 1, 2005, 23(10):2346-2357.
Dudley et al., "Cancer regression and autoimmunity in patients after clonal repopulation with antitumor lymphocytes," Science, Oct. 25, 2002, 298(5594):850-854.
Gendler et al., "Molecular cloning and expression of human tumor-associated polymorphic epithelial mucin," J. Biol. Chemistry, Sep. 5, 1990, 265(25):15286-15293.
Georgiannos et al., "The immunophenotype and activation status of the lymphocytic infiltrate in human breast cancers, the role of the major histocompatibility complex in cell mediated immune mechanisms, and their association with prognostic indicators," Surgery, Nov. 2003, 134(5):827-834.
Grommé et al., "Recycling MHC class I molecules and endosomal peptide loading," Proc. Natl. Acad. Sci. USA, Aug. 31, 1999, 96(18):10326-10331.
Hinrichs et al., "Adoptively transferred effector cells derived from naive rather than central memory CD8+ T cells mediate superior antitumor immunity," Proc. Natl. Acad. Sci. USA, Oct. 13, 2009, 106(41):17469-17474.
Hinrichs et al., "Type 17 CD8+ T cells display enhanced antitumor immunity," Blood, Jul. 16, 2009, 114(3):596-599.
Huang et al., "Sleeping Beauty transposon-mediated engineering of human primary T cells for therapy of CD19+ lymphoid malignancies," Mol. Therapy, Mar. 2008, 16(3):580-589.
Huang et al., "Survival, persistence, and progressive differentiation of adoptively transferred tumor-reactive T cells associated with tumor regression," J. Immunotherapy, May/Jun. 2005, 28(3):258-267.
Kalamasz et al., "Optimization of human T-cell expansion ex vivo using magnetic beads conjugated with anti-CD3 and Anti-CD28 antibodies," J. Immunotherapy, Sep./Oct. 2004, 27(5):405-418.
Katz et al., "T cell infiltrate predicts long-term survival following resection of colorectal cancer liver metastases," Ann. Surg. Oncology, Sep. 2009, 16(9):2524-2530.
Knutson et al., "IL-12 enhances the generation of tumour antigen-specific Th1 CD4 T cells during ex vivo expansion," Clin. Exp. Immunology, Feb. 2004, 135(2):322-329.
Kounis et al., "Attention to Infliximab adverse events: chimeric monoclonal antibodies can induce anti chimeric antibodies that may result in Kounis hypersensitivity associated acute coronary syndrome," Eur. Rev. Med. Pharmacol. Sciences, 2014, 18(24):3735-3736.
Lakshminarayanan et al., "Immune recognition of tumor-associated mucin MUC1 is achieved by a fully synthetic aberrantly glycosylated MUC1 tripartite vaccine," Proc. Natl. Acad. Sci. USA, Jan. 3, 2012, 109(1):261-266.
Laouar et al., "Concurrent generation of effector and central memory CD8 T cells during vaccinia virus infection," PLoS One, 2008, 3(12):e4089, 8 pages.
Life Technologies, "Dynabeads® Human T-Activator CD3/CD28: For activation of human T cells," SPEC-05780, 2011, 2 pages.
Maude et al., "Chimeric antigen receptor T cells for sustained remissions in leukemia," N. Engl. J. Medicine, Oct. 16, 2014, 371(16):1507-1517.
Moreno et al., "Anti-programmed cell death protein-1/ligand-1 therapy in different cancers," Br. J. Cancer, Apr. 28, 2015, 112(9):1421-1427.
Morgan et al., "Case report of a serious adverse event following the administration of T cells transduced with a chimeric antigen receptor recognizing ERBB2," Mol. Therapy, Apr. 2010, 18(4):843-851.
Morgan et al., "High efficiency TCR gene transfer into primary human lymphocytes affords avid recognition of melanoma tumor antigen glycoprotein 100 and does not alter the recognition of autologous melanoma antigens," J. Immunology, Sep. 15, 2003, 171(6):3287-3295.
Muranski et al., "Tumor-specific Th17-polarized cells eradicate large established melanoma," Blood, Jul. 15, 2008, 112(2):362-373.
Napolitani et al., "Selected Toll-like receptor agonist combinations synergistically trigger a T helper type 1-polarizing program in dendritic cells," Nat. Immunology, Aug. 2005, 6(8):769-776.

(56) References Cited

OTHER PUBLICATIONS

Porter et al., "A phase 1 trial of donor lymphocyte infusions expanded and activated ex vivo via CD3/CD28 costimulation," Blood, Feb. 15, 2006, 107(4):1325-1331.

Rosenberg et al., "Cancer immunotherapy: moving beyond current vaccines," Nat. Medicine, Sep. 2004, 10(9):909-915.

Sato et al., "Intraepithelial CD8+ tumor-infiltrating lymphocytes and a high CD8+/regulatory T cell ratio are associated with favorable prognosis in ovarian cancer," Proc. Natl. Acad. Sci. USA, Dec. 20, 2005, 102(51):18538-18543.

Shakushiro et al., "Efficient scavenger receptor-mediated uptake and cross-presentation of negatively charged soluble antigens by dendritic cells," Immunology, Jun. 2004, 112(2):211-218.

Siroy et al., "MUC1 is expressed at high frequency in early-stage basal-like triple-negative breast cancer," Hum. Pathology, Oct. 2013, 44(10):2159-2166.

Storkus et al., "Improving immunotherapy by conditionally enhancing MHC class I presentation of tumor antigen-derived Peptide epitopes," Crit. Rev. Immunology, 2007, 27(5):485-493.

Tran et al., "Minimally cultured tumor infiltrating lymphocytes display optimal characteristics for adoptive cell therapy," J. Immunotherapy, Oct. 2008, 31(8):742-751.

Weiner et al., "Vaccine prevention of cancer: can endogenous antigens be targeted?," Cancer Prev. Research, Apr. 2010, 3(4):410-415.

Xu et al., "Rapid high efficiency sensitization of CD8+ T cells to tumor antigens by dendritic cells leads to enhanced functional avidity and direct tumor recognition through an IL-12 dependent mechanism," J. Immunology, Sep. 1, 2003, 171(5):2251-2261.

Yannelli et al., "Growth of tumor-infiltrating lymphocytes from human solid cancers: summary of a 5-year experience," Int. J. Cancer, Feb. 8, 1996, 65(4):413-421.

METHODS AND MATERIALS FOR EXPANDING ANTIGEN-SPECIFIC T CELLS IN CULTURE

CLAIM OF PRIORITY

This application is a continuation of U.S. application Ser. No. 15/754,216, filed Feb. 21, 2018 know U.S. Pat. No. 10,647,961), which is a National Stage application under 35 U.S.C. § 371 of International Application No. PCT/US2016/046816, having an International Filing Date of Aug. 12, 2016, which claims the benefit of U.S. Provisional Application No. 62/208,263, filed Aug. 21, 2015. The disclosure of the prior applications are considered part of and are incorporated by reference in the disclosure of this application.

STATEMENT AS TO FEDERALLY SPONSORED RESEARCH

This invention was made with government support under CA136632 awarded by National Institutes of Health. The government has certain rights in the invention.

BACKGROUND

1. Technical Field

This document relates to methods and materials for expanding antigen-specific T cells (e.g., antigen-specific $CD4^+$ T cells and/or antigen-specific $CD8^+$ T cells) in culture. For example, this document provides methods and materials for performing a precisely initiated and a precisely terminated polyclonal stimulation step of such duration and intensity as to increase selectively the expansion and survival of T cells having a desired antigen specificity.

2. Background Information

There are many different therapeutic options for treating cancer. One promising approach is to obtain a cancer patient's blood and expand populations of active T cells that can be re-introduced into the cancer patient. It, however, has historically proved challenging to use peripheral blood as a T cell source for treating cancer.

SUMMARY

This document provides methods and materials for expanding antigen-specific T cells (e.g., antigen-specific $CD4^+$ T cells and/or antigen-specific $CD8^+$ T cells) in culture. For example, this document provides methods and materials for performing a polyclonal anti-CD3 stimulation step of precisely defined duration that is terminated after about 1 hour to about 48 hours (depending on the intensity of the stimulus) in order to further expand T cells having a desired antigen specificity. This is different from previous attempts where polyclonal anti-CD3 stimulation was initiated but not formally terminated, thereby leading to the death rather than expansion of the desired antigen-specific T-cell subpopulation.

As described herein, peripheral blood cells (e.g., peripheral blood mononuclear cells (PBMCs)) can be (a) obtained from a mammal (e.g., a human cancer patient), (b) treated without further fractionation in a first culture step that includes (i) promoting antigen presentation and (ii) exposing one or more desired antigens (e.g., an exogenously added antigen of interest) to T cells under conditions that activate T cells reactive against that desired antigen, (c) treated without further fractionation in a second culture that includes expanding the number of T cells reactive against the desired antigen, and (d) treated in a third culture step that includes polyclonally stimulating the T cells reactive against that desired antigen in a manner that promotes minimal, if any, cell death of those antigen-specific T cells, that promotes expansion of those antigen-specific T cells, and that promotes minimal, if any, activation of T cells reactive against irrelevant antigens (e.g., antigens other than the antigen(s) added in the first culture step). A fourth culture step can involve the continued expansion of antigen-specific T cells after the polyclonal stimulus is removed. For example, a population of cells that includes T cells that were stimulated against an antigen of interest and were expanded to increase their numbers can be exposed to a polyclonal stimulation step of defined duration under conditions wherein those antigen-specific T cells are expanded further and other T cells not reactive against the antigen of interest exhibit minimal, if any, expansion. In some cases, the polyclonal stimulation step can include contacting the cells with beads having anti-CD3 and anti-CD28 antibodies (e.g., Dynabeads obtained from Life Technologies, Inc.). Such methods can be used to obtain cell populations having large numbers of T cells reactive against a desired antigen with minimal numbers of active T cells that are reactive against antigens not of interest.

In general, one aspect of this document features a method for producing a cell population comprising T cells having specificity for an antigen of interest. The method comprises, or consists essentially of, (a) culturing a first cell population in the presence of beads comprising anti-CD3 antibodies and anti-CD28 antibodies for 1 hour to 48 hours to form a treated cell population, wherein the first cell population comprises T cells that were exposed to GM-CSF, resiquimod, E. coli lipopolysaccharide, and the antigen of interest for a first period of time and IL-7 for a second period of time, and (b) culturing the treated cell population in the absence of the beads for at least 3 days to form the cell population. The first cell population can comprise PBMCs exposed to GM-CSF, resiquimod, E. coli lipopolysaccharide, and the antigen of interest for the first period of time and IL-7 for the second period of time. The cells of the first cell population can be human cells. The anti-CD3 antibodies and the anti-CD28 antibodies can be covalently attached to the beads. The beads can have an average diameter between 4 µm and 5 µm. The GM-CSF can be a human GM-CSF. The antigen of interest can be a cancer-associated antigen. The cancer-associated antigen can be MUC1, HER2/neu, mesothelin, WT1, NYEso-1, MART1, gp100, or TRP. The IL-7 can be a human IL-7. The first period of time can be between about 16 hours and about 48 hours. The second period of time can be between about 9 days and about 11 days. The culturing of the first cell population in the presence of the beads can comprise culturing the first cell population in the presence of IL-7. The cell population can comprise greater than $0.5 \times 10^6$ $CD4^+$ T cells specific for the antigen of interest per million of cells of the first cell population. The cell population can comprise greater than $1 \times 10^6$ $CD4^+$ T cells specific for the antigen of interest per million of cells of the first cell population. The cell population can comprise greater than $0.15 \times 10^6$ $CD8^+$ T cells specific for the antigen of interest per million of cells of the first cell population. The cell population can comprise greater than $0.2 \times 10^6$ $CD8^+$ T cells specific for the antigen of interest per million of cells of the first cell population.

In another aspect, this document features a method for producing a cell population comprising T cells having specificity for an antigen of interest. The method comprises, or consists essentially of, (a) culturing a first cell population in the presence of immobilized anti-CD3 antibodies and soluble anti-CD28 antibodies for 1 hour to 48 hours to form a treated cell population, wherein the first cell population comprises T cells that were exposed to GM-CSF, resiquimod, *E. coli* lipopolysaccharide, and the antigen of interest for a first period of time and IL-7 for a second period of time, and (b) culturing the treated cell population in the absence of the immobilized anti-CD3 antibodies and the soluble anti-CD28 antibodies for at least 3 days to form the cell population. The first cell population can comprise PBMCs exposed to GM-CSF, resiquimod, *E. coli* lipopolysaccharide, and the antigen of interest for the first period of time and IL-7 for the second period of time. The cells of the first cell population can be human cells. The GM-CSF can be a human GM-CSF. The antigen of interest can be a cancer-associated antigen. The cancer-associated antigen can be MUC1, HER2/neu, mesothelin, WT1, NYEso-1, MART1, gp100, or TRP. The IL-7 can be a human IL-7. The first period of time can be between about 16 hours and about 48 hours. The second period of time can be between about 9 days and about 11 days. The culturing of the first cell population in the presence of the immobilized anti-CD3 antibodies and soluble anti-CD28 antibodies can comprise culturing the first cell population in the presence of IL-7. The cell population can comprise greater than $3\times10^6$ CD4$^+$ T cells specific for the antigen of interest per million of cells of the first cell population. The cell population can comprise greater than $4\times10^6$ CD4$^+$ T cells specific for the antigen of interest per million of cells of the first cell population. The cell population can comprise greater than $5\times10^6$ CD4$^+$ T cells specific for the antigen of interest per million of cells of the first cell population. The cell population can comprise greater than $1.5\times10^6$ CD8$^+$ T cells specific for the antigen of interest per million of cells of the first cell population. The cell population comprises greater than $2\times10^6$ CD8$^+$ T cells specific for the antigen of interest per million of cells of the first cell population.

In another aspect, this document features a method for producing a cell population comprising T cells having specificity for an antigen of interest. The method comprises, or consists essentially of, (a) exposing a cell population comprising T cells to GM-CSF, resiquimod, *E. coli* lipopolysaccharide, and an antigen of interest for a first period of time, (b) exposing the cell population to IL-7 for a second period of time, (c) exposing the cell population to (i) immobilized anti-CD3 antibodies and soluble anti-CD28 antibodies or (ii) beads comprising anti-CD3 antibodies and anti-CD28 antibodies for a third time period to form a treated cell population, and (d) culturing the treated cell population in the absence of (i) the immobilized anti-CD3 antibodies and soluble anti-CD28 antibodies and (ii) the beads for a fourth period of time to produce a final cell population comprising T cells having specificity for the antigen of interest. The cell population can comprise PBMCs. The cells of the cell population can be human cells. The GM-CSF can be a human GM-CSF. The antigen of interest can be a cancer-associated antigen. The cancer-associated antigen can be MUC1, HER2/neu, mesothelin, WT1, NYEso-1, MART1, gp100, or TRP. The antigen of interest can be a pathogen-associated antigen. The pathogen-associated antigen can be a cytomegalovirus, Epstein-Barr virus, human papilloma virus, *Mycobacterium tuberculosis*, *Candida albicans*, aspergillis, *Mycobacterium avian intracellularis*, Ebola virus, or HIV antigen. The IL-7 can be a human IL-7. The first period of time can be between about 16 hours and about 48 hours. The second period of time can be between about 9 days and about 11 days. The third period of time can be between about 1 hour and about 48 hours. The fourth period of time can be between about 6 days and about 10 days. The method can comprise exposing the cell population to the immobilized anti-CD3 antibodies and the soluble anti-CD28 antibodies. The final cell population can comprise greater than $3\times10^6$ CD4$^+$ T cells specific for the antigen of interest per million of cells of the cell population. The final cell population can comprise greater than $4\times10^6$ CD4$^+$ T cells specific for the antigen of interest per million of cells of the cell population. The final cell population can comprise greater than $5\times10^6$ CD4$^+$ T cells specific for the antigen of interest per million of cells of the cell population. The final cell population can comprise greater than $1.5\times10^6$ CD8$^+$ T cells specific for the antigen of interest per million of cells of the cell population. The final cell population can comprise greater than $2\times10^6$ CD8$^+$ T cells specific for the antigen of interest per million of cells of the cell population. The method can comprise exposing the cell population to the beads. The anti-CD3 antibodies and the anti-CD28 antibodies can be covalently attached to the beads. The beads can have an average diameter between 4 μm and 5 μm. The final cell population can comprise greater than $0.5\times10^6$ CD4$^+$ T cells specific for the antigen of interest per million of cells of the cell population. The final cell population can comprise greater than $1\times10^6$ CD4$^+$ T cells specific for the antigen of interest per million of cells of the cell population. The final cell population can comprise greater than $0.15\times10^6$ CD8$^+$ T cells specific for the antigen of interest per million of cells of the cell population. The final cell population can comprise greater than $0.2\times10^6$ CD8$^+$ T cells specific for the antigen of interest per million of cells of the cell population.

In another aspect, this document features a method for providing a mammal with T cells having specificity for an antigen of interest. The method comprises, or consists essentially of, administering a cell population produced as set forth in any of the preceding three paragraphs. The mammal can be a human. The cell population can be a cell population produced from PBMCs obtained from the mammal.

In another aspect, this document features a method for producing a cell population comprising T cells having specificity for an antigen of interest. The method comprises, or consists essentially of, (a) a polyclonal stimulation of cultured T-cells with anti-CD3 antibody subsequent to stimulation with a specific antigen of interest, wherein the polyclonal stimulation is terminated after a time period to avoid lethal overstimulation of antigen-specific T-cells and to avoid activation of bystander T-cells that recognize irrelevant antigens, and (b) further culturing the cultured T-cells following removal of the polyclonal stimulation to further increase yields of antigen-specific T-cells. The polyclonal stimulation can comprise using beads or matrix comprising covalently bound or non-covalently-bound anti-CD3 antibodies and optionally anti-CD28 antibodies. The polyclonal stimulation can comprise using soluble or immobilized anti-CD3 antibodies and optionally anti-CD28 antibodies. The cultured T-cells used in step (a) can be present within an unfractionated PBMC preparation that was exposed to GM-CSF, the antigen of interest, a Toll-like receptor 8 agonist, and a Toll-like receptor 4 agonist, followed by exposure to IL-7. The antigen of interest can be a cancer-associated antigen. The cancer-associated antigen can be MUC1, HER2/neu, mesothelin, WT1, NYEso-1, MART1, gp100, or TRP, or tumor cells processed by freeze/thawing, irradiation, homogenization, or heat killing. The antigen of interest can be a pathogen-associated antigen. The pathogen-associated antigen can be a cytomegalovirus, Epstein-Barr virus, human papilloma virus, *Mycobacterium tuberculosis, Candida albicans*, aspergillis, *Mycobacterium* avian *intracellularis*, Ebola virus, or HIV antigen.

In another aspect, this document features a method for producing a cell population comprising T cells having specificity for an antigen of interest. The method comprises, or consists essentially of, (a) exposing a cell population comprising T cells to GM-CSF, an antigen of interest, resiquimod, and *E. coli* lipopolysaccharide for a first period of time, (b) exposing the cell population to IL-7 for a second period of time, (c) while optionally continuing IL-7 exposure, exposing the cell population to (i) immobilized anti-CD3 antibodies and soluble anti-CD28 antibodies or (ii) beads or matrix comprising anti-CD3 antibodies and anti-CD28 antibodies for a third period of time to expand antigen-specific T cells, thereby forming a treated cell population, and (d) culturing the treated cell population in the absence of (i) the immobilized anti-CD3 antibodies and soluble anti-CD28 antibodies and (ii) the beads for at least 5 days to produce a final cell population comprising T cells having specificity for the antigen of interest. The cell population can comprise unfractionated PBMCs. The cells of the cell population can be human cells. The GM-CSF can be a human GM-CSF. The antigen of interest can be a cancer-associated antigen. The cancer-associated antigen can be MUC1, HER2/neu, mesothelin, WT1, NYEso-1, MART1, gp100, or TRP, or tumor cells processed by freeze/thawing, irradiation, homogenization, or heat killing. The antigen of interest can be a pathogen-associated antigen. The pathogen-associated antigen can be a cytomegalovirus, Epstein-Barr virus, human papilloma virus, *Mycobacterium tuberculosis, Candida albicans*, aspergillis, *Mycobacterium* avian *intracellularis*, Ebola virus, or HIV antigen. The IL-7 can be a human IL-7. The first period of time can be between about 16 hours and about 48 hours. The second period of time can be between about 9 days and about 11 days. The third period of time can be between about 1 hour and about 48 hours. The at least 5 days can be from about 6 days to about 10 days.

In another aspect, this document features a method for providing a mammal with T cells having specificity for an antigen of interest, wherein the method comprises administering a cell population produced as set forth in any of the preceding two paragraphs. The mammal can be a human. The cell population can be a cell population that was produced from unfractionated PBMCs obtained from the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and from the claims.

DESCRIPTION OF THE DRAWINGS

FIG. 1 is as described elsewhere (Knutson and Disis, *Clin. Exp. Immunol.*, 135:322-329 (2004)).

DETAILED DESCRIPTION

Figure 1:
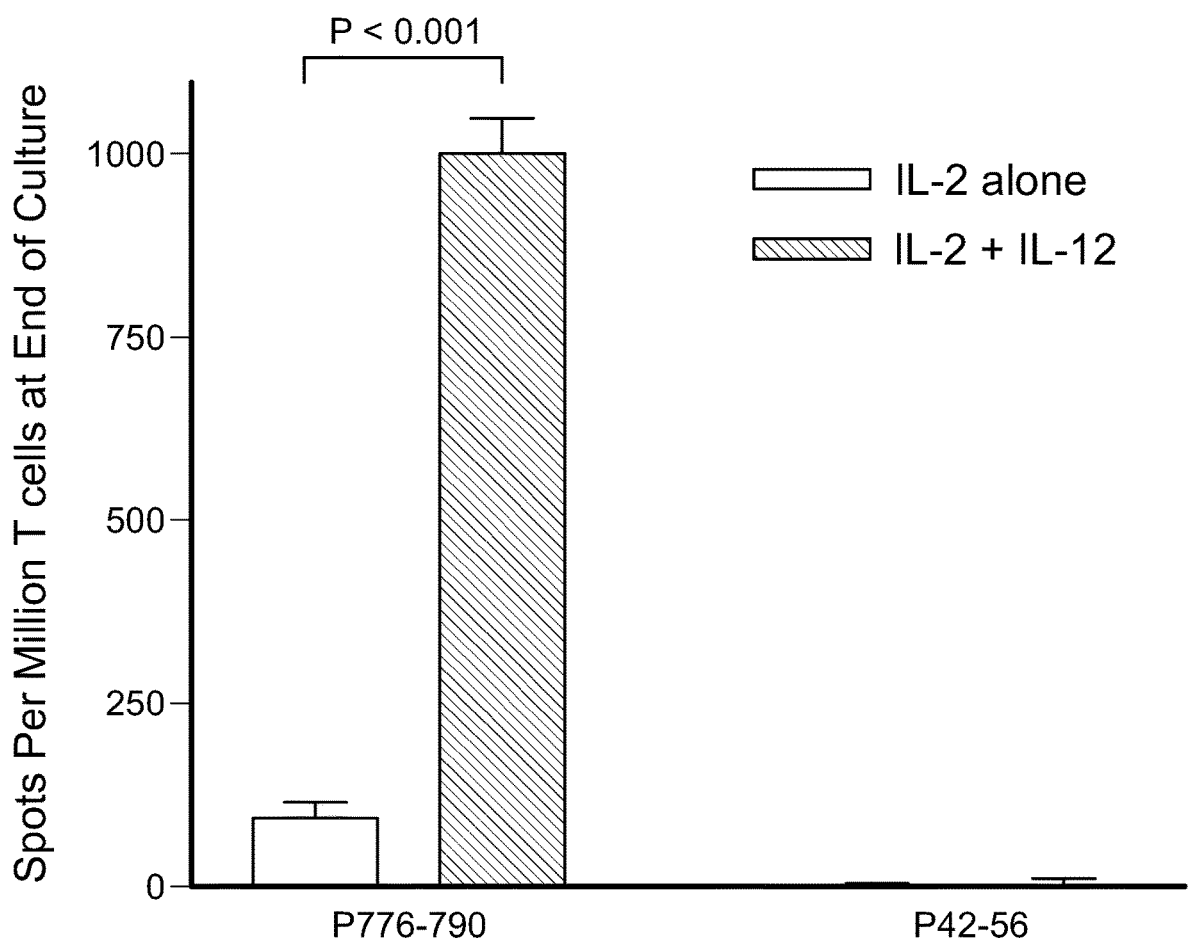
FIG. 1. IL-12 is needed to expand Her2 specific Th1 ex vivo. PBMCs from a representative patient recently vaccinated with p776-790 15-mer, but not p42-56, were cultured with p776-790+rIL-2, with or without rIL-12, for 12 days, after which T-cells were re-exposed to the relevant or irrelevant peptide in an IFN-g ELISPOT assay. The frequency of p776-790 specific T-cells increased only from 0.0001% to 0.001%. This

This document provides methods and materials for producing antigen-specific T cells (e.g., antigen-specific CD4$^+$ T cells and/or antigen-specific CD8$^+$ T cells). For example, this document provides methods and materials for performing a polyclonal stimulation step of defined duration (e.g., typically ranging from one hour to about 24 hours depending on the stimulus' intensity) to further increase the expansion of T cells having a desired antigen specificity.

As described herein, peripheral blood cells (e.g., unfractionated peripheral blood mononuclear cells (PBMCs)) can be obtained from a mammal (e.g., a healthy human or a human cancer patient such as a human with advanced cancer). Examples of other cell populations that can be obtained and used as described herein to make populations of antigen-specific T cells (e.g., antigen-specific $CD4^+$ T cells and/or antigen-specific $CD8^+$ T cells) include, without limitation, tumor, lymph node, spleen, bone marrow, cerebrospinal fluid, pleural fluid, peritoneal fluid, and joint fluid samples that contain cells. Once obtained, the cells can initially be cultured in a manner that promotes antigen presentation. For example, unfractionated PBMC can be exposed to GM-CSF, the Toll-like receptor 8 agonist resiquimod, the Toll-like receptor 4 agonist E. coli lipopolysaccharide (LPS), or combinations thereof, with or without interpolated exposure to the antigen(s) of interest. In some cases, the cells can be exposed to GM-CSF, resiquimod, and E. coli lipopolysaccharide. The amount of GM-CSF can be from about 10 ng/mL to about 100 ng/mL (e.g., about 40 ng/mL). The amount of resiquimod can be from about 1 µg/mL to about 9 µg/mL (e.g., about 3 µg/mL). The amount of E. coli lipopolysaccharide can be from about 1 ng/mL to about 50 ng/mL (e.g., about 5 ng/mL). Other TLR8 agonists (e.g., motolimod) can be used in place of or in addition to resiquimod. Other TLR4 agonists (e.g., *salmonella* lipopolysaccharide) can be used in place of or in addition to E. coli LPS. In some cases, interferon-gamma and/or other TLR agonists such as poly I:C (TLR3 agonist) can be substituted for the Toll-like Receptor 4 or 8 agonist. The cells can be exposed to one or more agents designed to promote antigen presentation (e.g., GM-CSF, resiquimod, and E. coli lipopolysaccharide) for any appropriate length of time. For example, effective presentation of antigen(s) added to culture can be achieved by first exposing unfractionated PBMC to GM-CSF alone for 18-24 hours, then the next day adding the antigen(s) of interest, then four hours later adding resiquimod and 30 minutes later adding lipopolysaccharide for an additional 16-30 hours before moving into step 2 of culture.

While treating the unfractionated PBMCs in a manner that promotes antigen presentation, the cells can be exposed to one or more desired antigens under conditions that activate T cells reactive against that desired antigen(s). The first step of culture can be pulsed with any appropriate antigen of interest. For example, cancer-associated antigens such as peptide sequences derived from MUC1, HER2/neu, or mesothelin, or processed tumor cells themselves (e.g., freeze-thawed lysates) or combinations thereof can be placed in contact with the cells. The amount of peptide antigen can be from about 5 µg/mL to about 100 g/mL (typically about 10-50 µg/mL). The cells can be exposed to one or more desired antigens for any appropriate length of time. For example, the cells can be exposed to one or more desired antigens for about 1 hour to about 24 hours. In some cases, the cells can be treated in a manner that promotes antigen presentation and exposure to one or more desired antigens concurrently. For example, the cells can be exposed to GM-CSF, an antigen(s) of interest, resiquimod, and E. coli lipopolysaccharide in that sequence within the first 36-60 hours of PBMC culture.

After treating the unfractionated PBMCs in a manner that promotes antigen presentation and exposing the cells to at least one antigen of interest, the cells can be exposed to IL-7 as the next step of culture to preferentially expand the T-cell subpopulation within unfractionated PBMCs which recognizes the pulsed antigen(s) of interest. The amount of IL-7 can be from about 5 ng/mL to about 100 ng/mL (e.g., about 10 ng/mL every three days or about 50 ng/mL in added fresh medium). The cells can be exposed to IL-7 for any appropriate length of time. For example, the cells can be exposed to IL-7 for about 10-22 days (e.g., about 17-19 days).

After treating the cells in a manner that promotes antigen presentation, exposing the cells to at least one antigen of interest, and exposing the cells to IL-7, the cells can be exposed to (i) immobilized anti-CD3 antibodies and soluble anti-CD28 antibodies and/or (ii) beads or matrix containing anti-CD3 antibodies and anti-CD28 antibodies. Examples of beads or matrix containing anti-CD3 antibodies and anti-CD28 antibodies include, without limitation, Dynabeads (obtained from Life Technologies, Inc.) and Miltenyi MACS GMP TransAct CD3/CD28 matrix). Dynabeads containing anti-CD3 and anti-CD28 antibodies and having diameters of about 4.5 µm can be used as described herein. The ratio of cells (cultured PBMCs) to beads can be from about 1:1 to about 6:1. When using immobilized anti-CD3 antibodies, the amount of immobilized anti-CD3 antibodies can be from about 0.1 µg/mL to about 10 µg/mL (e.g., about 0.3 µg/mL). When using soluble anti-CD28 antibodies, the amount of soluble anti-CD28 antibodies can be from about 0.1 µg/mL to about µg/mL (e.g., about 1 µg/mL).

The cells can be exposed to (i) immobilized anti-CD3 antibodies and soluble anti-CD28 antibodies and/or (ii) beads or matrix containing anti-CD3 antibodies and anti-CD28 antibodies beginning on any appropriate day of culture. For example, the cells can be exposed to immobilized anti-CD3 antibodies and soluble anti-CD28 antibodies on day 12 of culture. The cells can be exposed to (i) immobilized anti-CD3 antibodies and soluble anti-CD28 antibodies and/or (ii) beads or matrix containing anti-CD3 antibodies and anti-CD28 antibodies for any appropriate length of time. For example, the cells can be exposed to immobilized anti-CD3 antibodies and soluble anti-CD28 antibodies for from about 1 hours to about 48 hours. In some cases, the cells are not exposed to immobilized anti-CD3 antibodies and soluble anti-CD28 antibodies for more than 4 hours. In some cases, the cells can be exposed to beads containing anti-CD3 antibodies and anti-CD28 antibodies for from about 1 hour to about 48 hours. In some cases, the cells are not exposed to beads containing anti-CD3 antibodies and anti-CD28 antibodies for more than 4 hours. In some cases, the more beads added, the shorter the exposure can be to avoid lethally overstimulating the desired antigen-specific T-cell subpopulation.

After exposing the cells to (i) immobilized anti-CD3 antibodies and soluble anti-CD28 antibodies and/or (ii) beads containing anti-CD3 antibodies and anti-CD28 antibodies, the cells are washed or treated in a manner that removes the immobilized anti-CD3 antibodies, soluble anti-CD28 antibodies, and beads containing anti-CD3 antibodies and anti-CD28 antibodies. For example, beads that are magnetic can be removed from the cells using a magnet.

After removing the cells from exposure to immobilized anti-CD3 antibodies, soluble anti-CD28 antibodies, and/or beads containing anti-CD3 antibodies and anti-CD28 antibodies, the cells can continue to be cultured (i) in the absence of immobilized anti-CD3 antibodies and soluble anti-CD28 antibodies and (ii) in the absence of beads containing anti-CD3 antibodies and anti-CD28 antibodies. The cells can continue to be cultured in the absence of (i)

immobilized anti-CD3 antibodies and soluble anti-CD28 antibodies and (ii) beads containing anti-CD3 antibodies and anti-CD28 antibodies for any appropriate length of time. For example, the cells can be cultured in the absence of (i) immobilized anti-CD3 antibodies and soluble anti-CD28 antibodies and (ii) beads containing anti-CD3 antibodies and anti-CD28 antibodies for from about 7 days to about 11 days. In some cases, the cells can be cultured in the absence of (i) immobilized anti-CD3 antibodies and soluble anti-CD28 antibodies and (ii) beads containing anti-CD3 antibodies and anti-CD28 antibodies for longer than 11 days.

Once a population of antigen-specific T cells (e.g., antigen-specific CD4+ T cells and/or antigen-specific CD8+ T cells) is obtained as described herein, the cells can be administered to a mammal for use in, for example, adoptive cellular therapies to treat infections and/or cancer. Any appropriate mammal can be treated with the antigen-specific T cells (e.g., antigen-specific CD4+ T cells and/or antigen-specific CD8+ T cells) provided herein. For example, humans, horses, cattle, pigs, dogs, cats, mice, and rats can be treated with a population of antigen-specific T cells (e.g., antigen-specific CD4+ T cells and/or antigen-specific CD8+ T cells). In some cases, any appropriate number of antigen-specific T cells (e.g., antigen-specific CD4+ T cells and/or antigen-specific CD8+ T cells) provided herein can be administered to a mammal. For example, between about $1\times10^3$ cells and about $1-2\times10^{11}$ T cells including antigen-specific T-cells can be administered to a mammal. Any appropriate route of administration can be used to administer the antigen-specific T cells provided herein to a mammal. For example, antigen-specific T cells can be administered intravenously, intraperitoneally, subcutaneously, intramuscularly, intrahepatically, or intranodally.

The invention will be further described in the following examples, which do not limit the scope of the invention described in the claims.

EXAMPLES

Example 1—Generating Populations of Antigen-Specific T Cells from PBMCs

Figure 2:
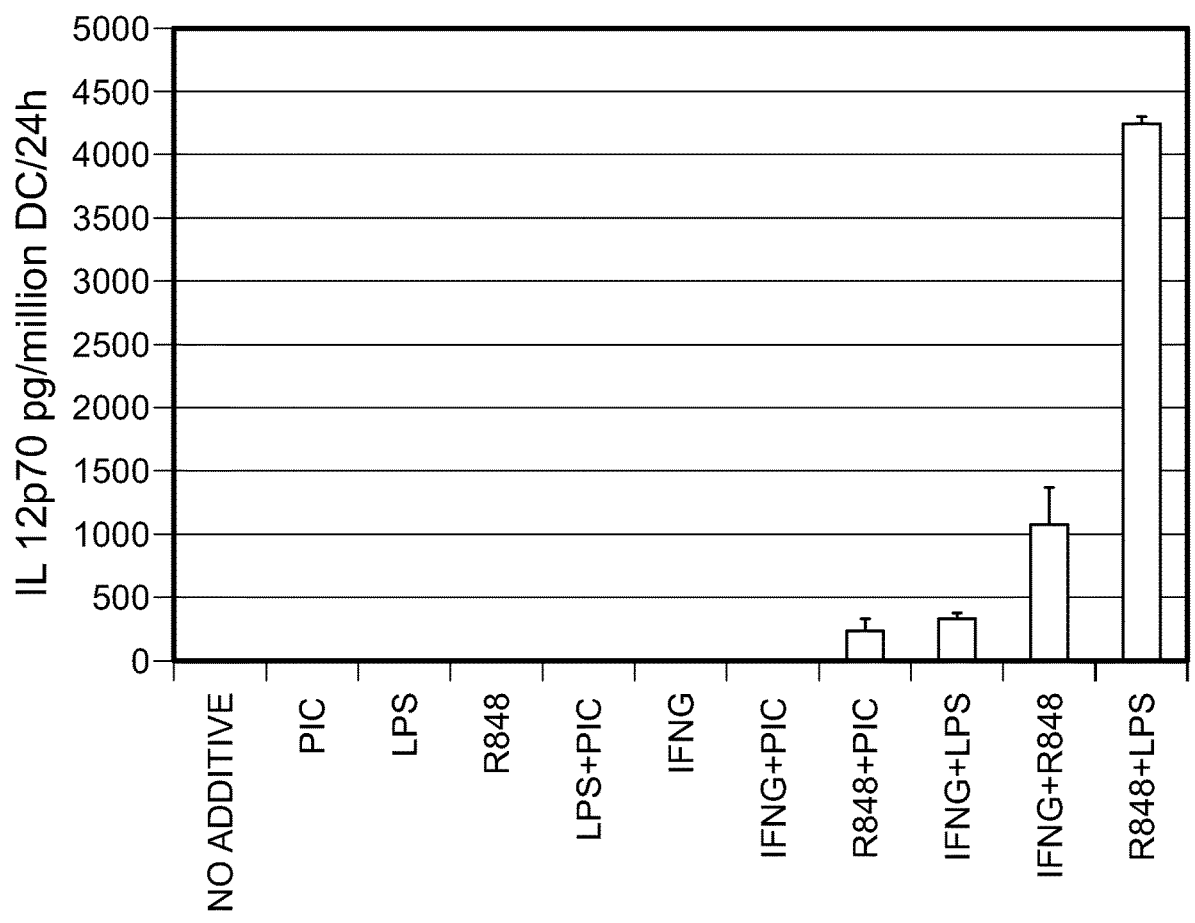
FIG. 2. DC1 polarization in cryopreserved PBMC. Thawed PBMCs were cultured overnight in GM-CSF, then treated with various TLR agonists or IFN-γ, followed by ELISA. Representative of 14 different healthy and cancer patients.
Figure 3:
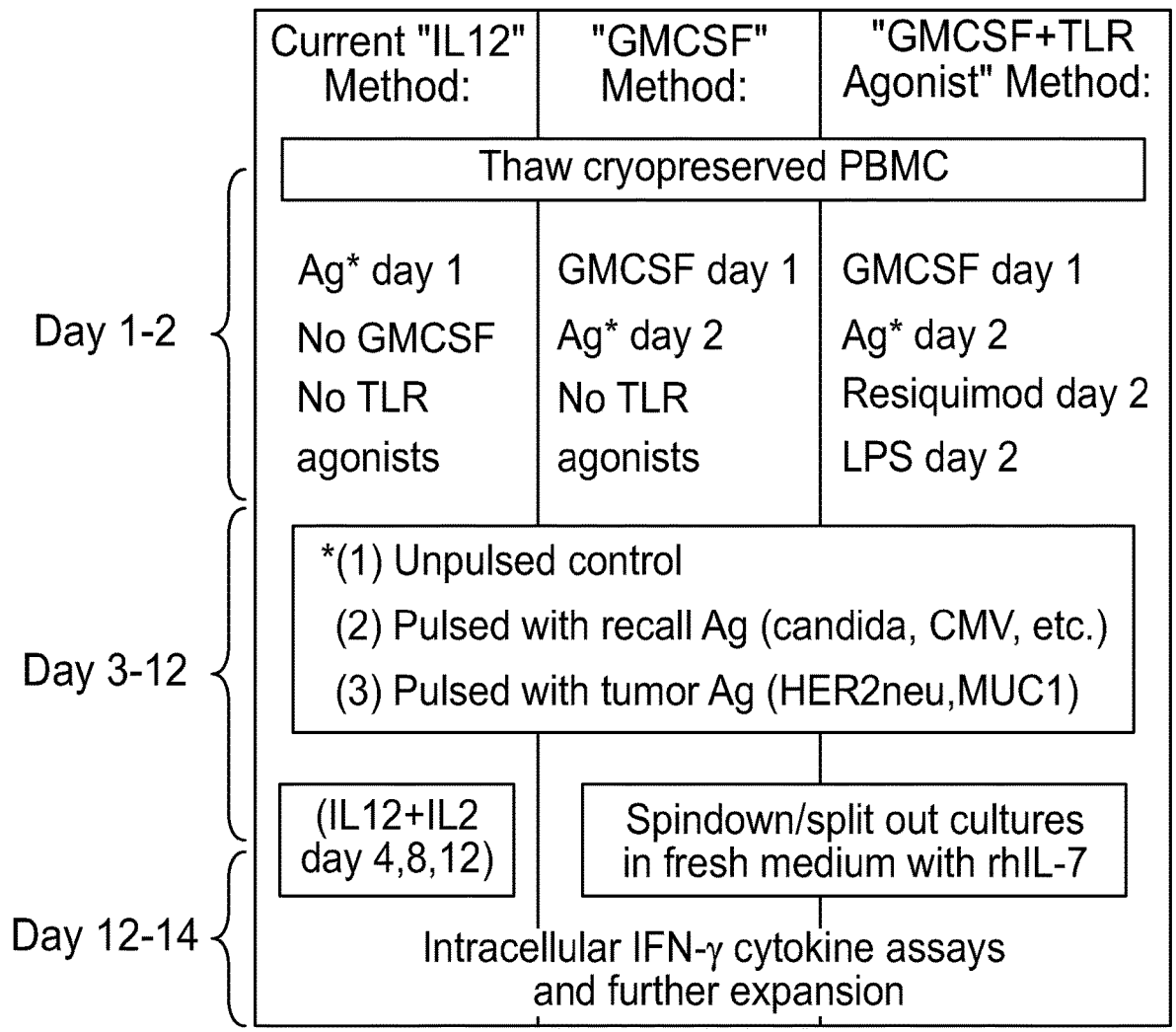
FIG. 3 contains a table of culture comparison schema.

IL-12 was shown previously to be needed to expand Her2-specific Th1 ex vivo (FIG. 1). Hypothesizing that exogenous rIL-12 might not provide the full benefit of DC1 polarization to T cell cultures, the following was performed to achieve natural DC1 polarization, with IL12p70 production, within bulk PBMC cultures. Even though a variety of paired danger signals can effectively DC1-polarize purified fresh human DCs (e.g., LPS+IFN-γ), most such signals proved surprisingly ineffective for activating robust IL-12 production in unfractionated PBMCs. Only overnight exposure to GM-CSF, followed by combined exposure to TLR4+TLR8 agonists (LPS+resiquimod (R848)) was consistently effective to DC1-polarize unfractionated human PBMC, whether fresh or cryopreserved (FIG. 2). This "GM+TLR" culturing method was compared to culturing methods omitting resiquimod+LPS ("GM") and compared to culturing methods that use exogenous IL-12, but without GM-CSF or TLR agonists ("IL-12" as in FIG. 1) (FIG. 3). Cryopreserved leukapheresed PBMCs from multiple healthy donors were repetitively tested for their ability to give rise to T1-type CD4+ and CD8+ T-cells specifically reactive to clinical-grade *Candida* extract (CAN) or HER2 intracellular domain protein (ICD) after 1 or 2 rounds of Ag-driven culture. The following was observed.

Figure 4:
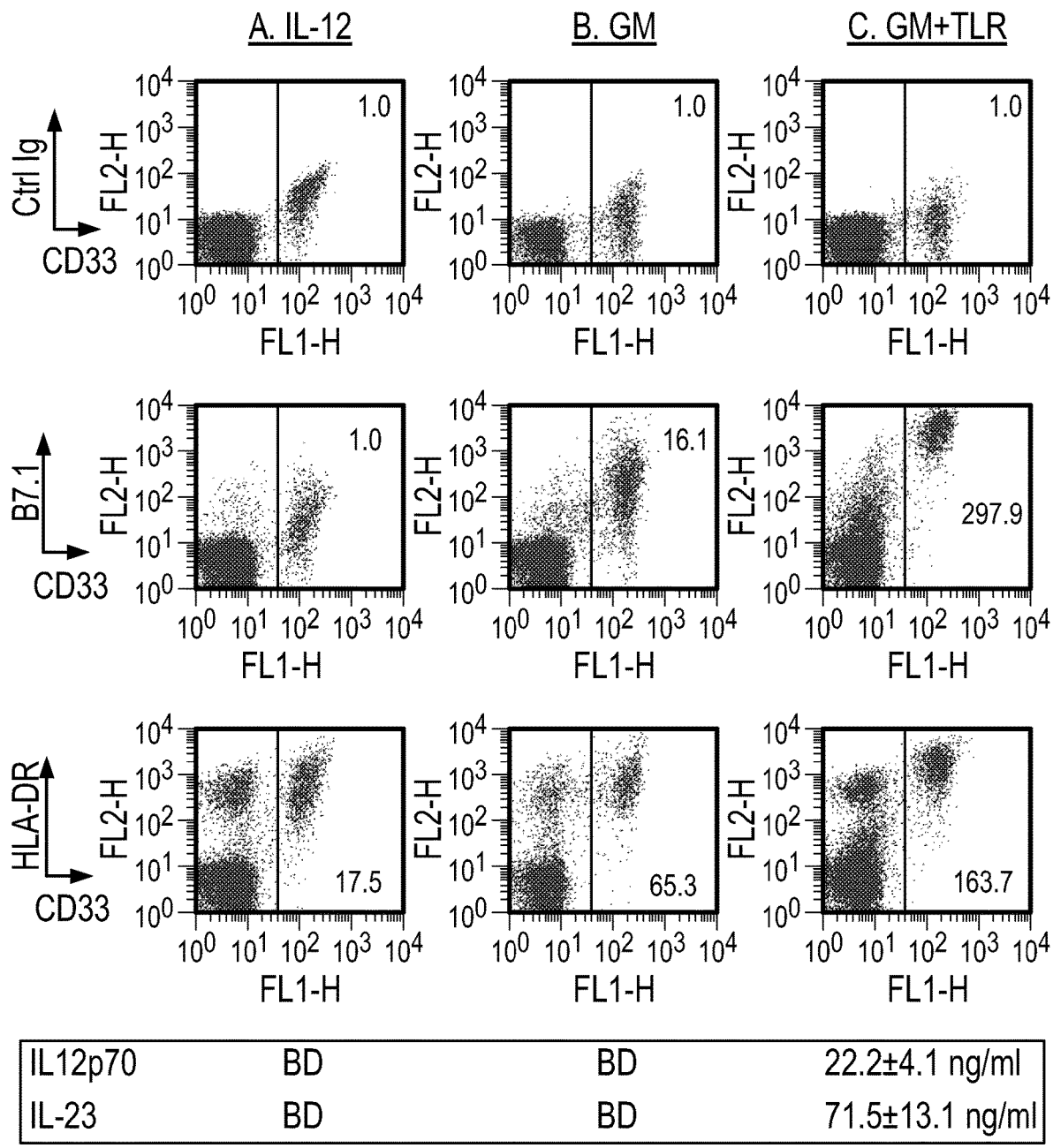
FIG. 4. PBMC pulsed with GM-CSF then resiquimod+LPS (GM+TLR) display superior DC activation. Representative of 3 donors and 3 different Ag pulses per donor (*Candida*, HER2 intracellular domain (ICD), or ICD-derived 15mer (latter not shown)). At 48 hours, all CD33$^+$ cells also expressed the DC marker CD11c (not shown). Every GM+TLR treated ("C") group displayed upregulated HLA-DR and B7.1. In contrast, DCs in GM ("B") or IL12 ("A") groups were heterogeneously activated and in some cases minimally activated for B7.1 or HLA-DR. Numbers within dot plots show mean Y-axis fluorescent index of the CD33$^+$ subpopulation. Each shown IL12p70 or IL23 determination is the average for all donors and Ags for A, B, or C culture conditions (n=9 for each condition). BD=below detection (<75 pg/mL).
Figure 5:
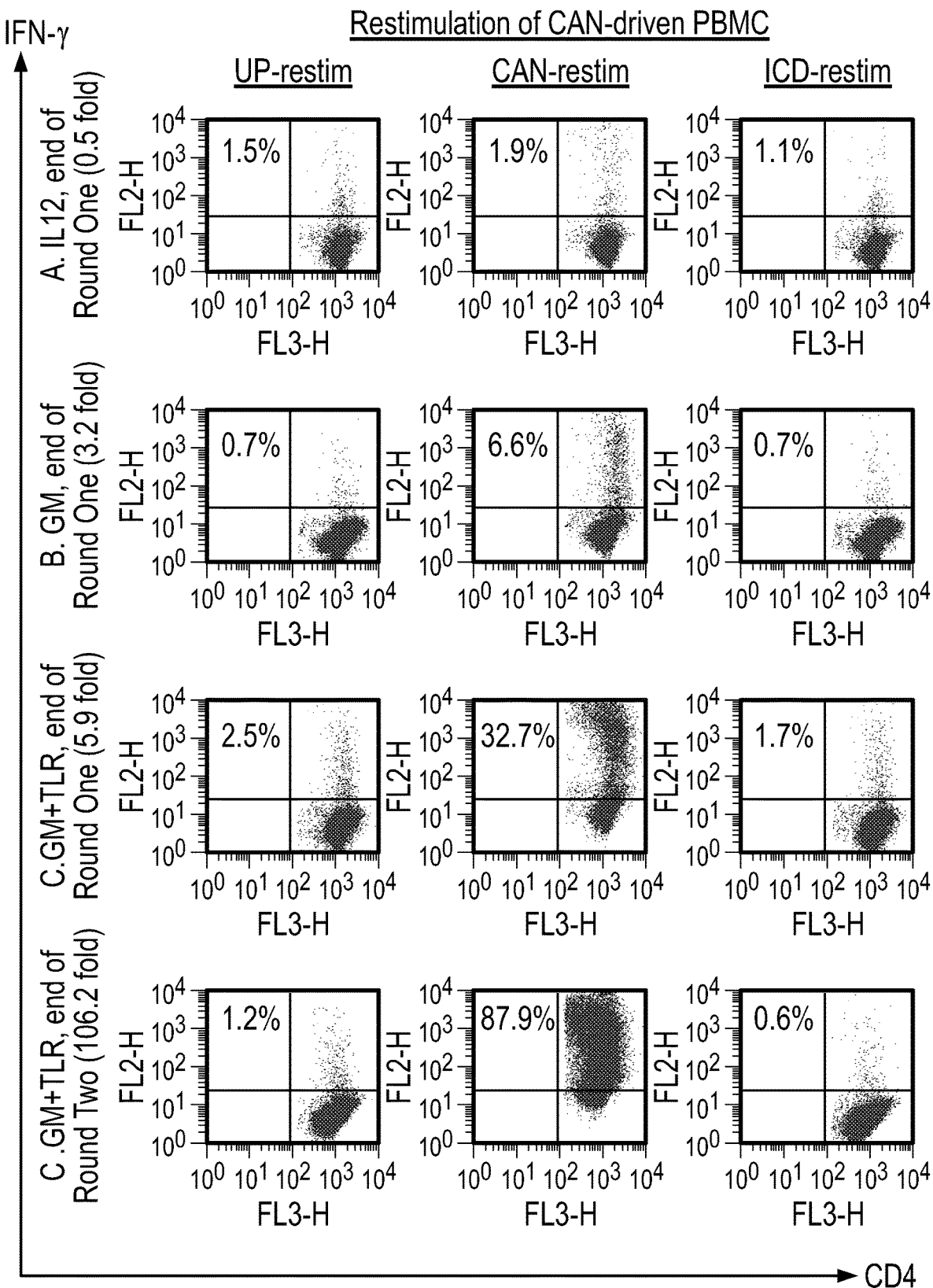
FIG. 5. Representative dot plots for a healthy donor's PBMC CAN- and ICD-driven groups. IL12 vs GM vs GM+TLR culture conditions were compared by an intracellular cytokine assay (ICC) at the end of Round One, and also to a Round Two continuation of the "GM+TLR" groups (resiquimod+LPS omitted after round 1). Only the CD4 window is shown. % shown within each dotplot is the % of all CD4$^+$ T cells producing IFN-γ following exposure to freshly thawed PBMC either unpulsed (UP) or CAN- or ICD-pulsed. Parallel trends were observed regarding CD8$^+$ T cell sensitization (not shown).
Figure 5:
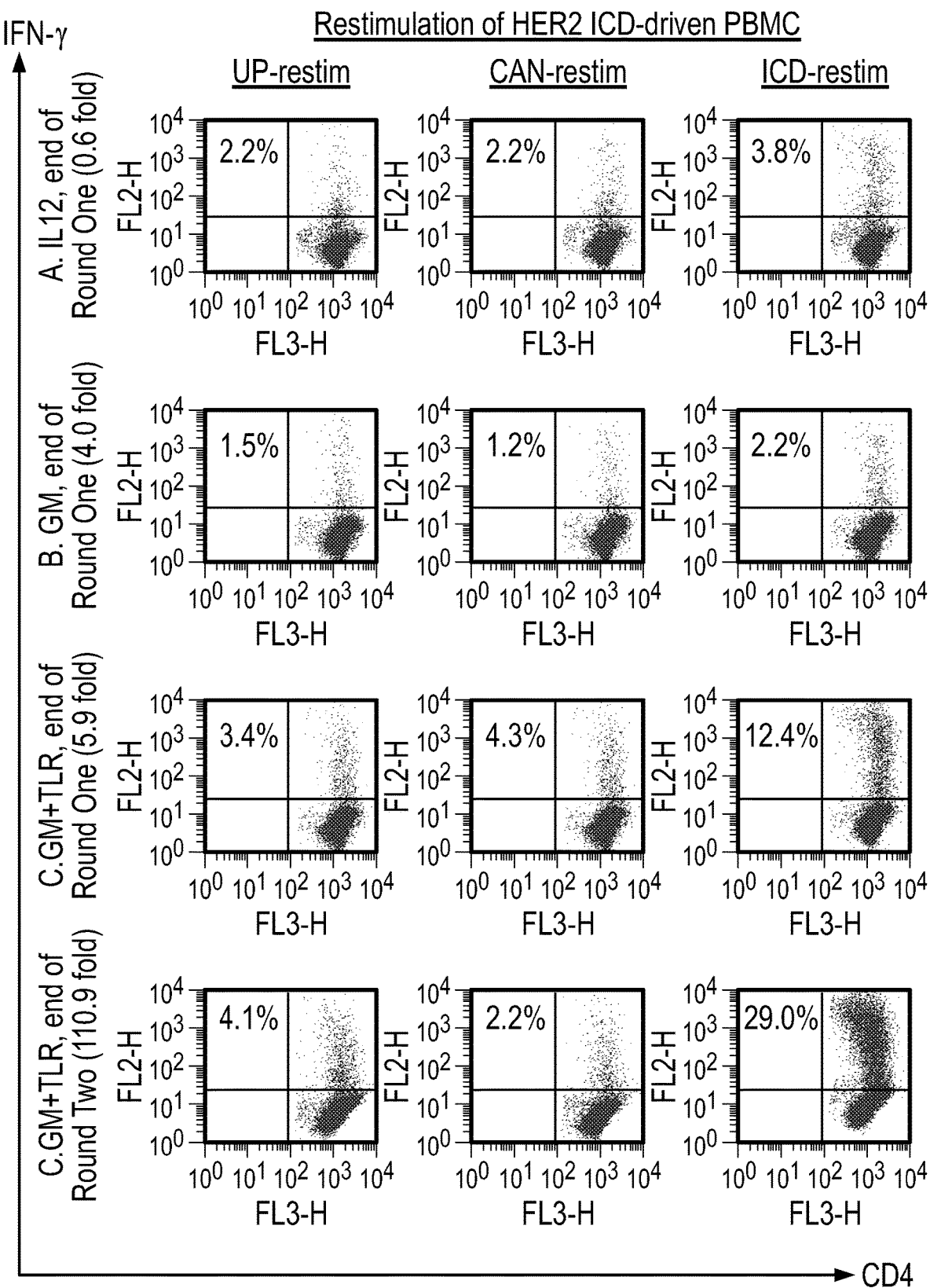

Only GM+TLR cultures displayed consistent DC upregulation of MHC and costimulatory molecules (FIG. 4). Only GM+TLR cultures produced IL12p70 and IL-23 (FIG. 4). Ag-pulsed GM+TLR cultures significantly outperformed Ag-pulsed GM and IL-12 cultures in: fold-expansion, Ag-specific frequency, and total yield of Ag-specific T1 (IFN-γ+) cells, both CD4+ and CD8+, by the end of round 1 culture (FIG. 5). The frequency of HER2-specific, IFN-γ producing T cells at the end of Round 1 culture was 9.0%±2.1 of CD4+ and 4.1±1.5% of CD8+ cells, with a further surge in specificity typically seen following a second round of Ag-pulsed DC-driven culture (FIG. 5). This robust Ag-specific enrichment of both CD4+ and CD8+ T cells was often achievable within GM+TLR cultures even without prior vaccination to CAN or Her2Neu.

Besides enriching for HER2-specificity, two rounds of optimized DC-driven culture resulted in 100-400-fold T cell numeric expansion, allowing $10^{11}$ or more T cells enriched for HER2-specificity to be prepared from merely $10^9$ PBMCs.

Figure 6:
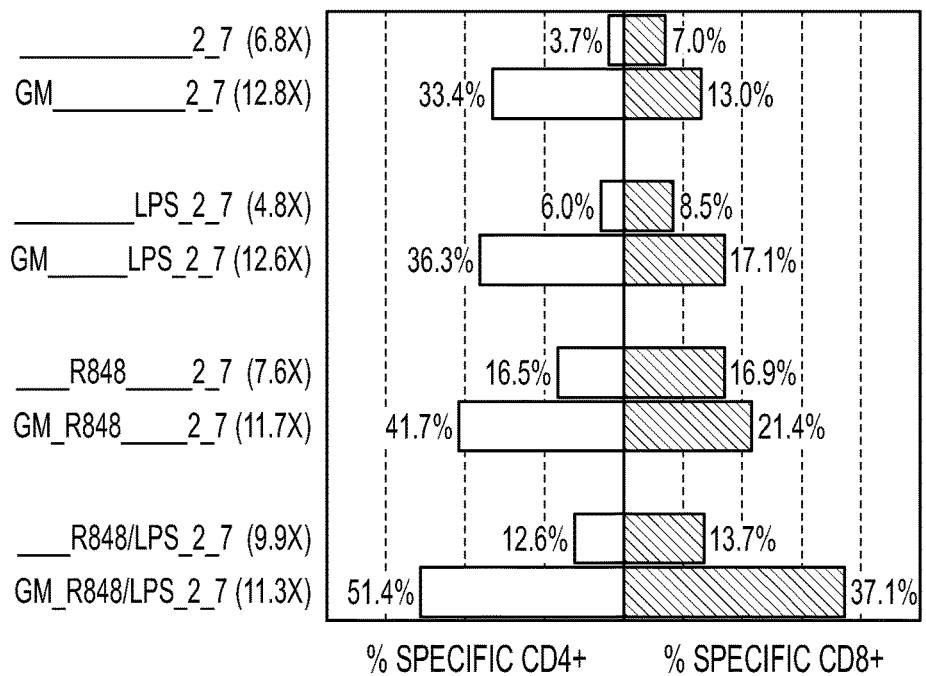
FIG. 6. Impact of GM-CSF and IL-7 on GM+TLR culture method's enrichment of Ag-specific frequency. A. Individual wells of PBMCs received or did not receive rGM-CSF day 0 ("GM"). All groups received *Candida* (CAN) day 1, and variably received LPS and/or R848. All groups expanded in IL7/IL2 ("2_7"). Re-stimulation occurred 2 weeks later. Fold proliferation is shown. Graph shows calculated frequency of CAN-specific IFN-γ producing CD4$^+$ (left) and CD8$^+$ (right) T-cells. B. All PBM5C cultures received GM day 0, CAN, R848, and LPS day 1, and variably IL2, IL-7, IL-15, and/or IL-21 (2, 7, 15, 21) day 2 through 15. Fold proliferation is shown.
Figure 6:
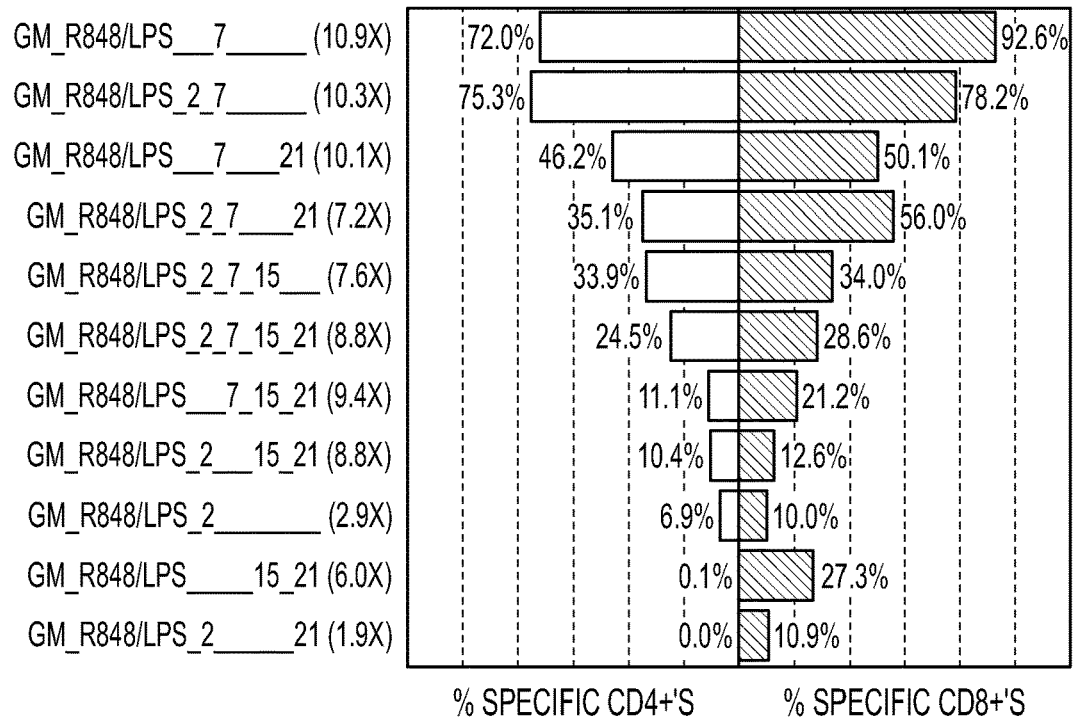

Maximally enriched Ag-specificity in PBMC T cell cultures at this stage appeared to require GM-CSF and IL-7 and TLR agonist exposure (FIG. 6). Omitting dual TLR agonists effectively halved the proportion of Ag-specific CD8+ T-cells, and omitting GM-CSF effectively cut the proportion of Ag-specific CD4+ T-cells by a third. Omitting IL-7 effectively drove specificity down by a log. Furthermore, factors such as IL-21, IL-15, and IL-4 relatively impaired the development of enriched T cell specificity compared to IL-7 alone.

Figure 7:
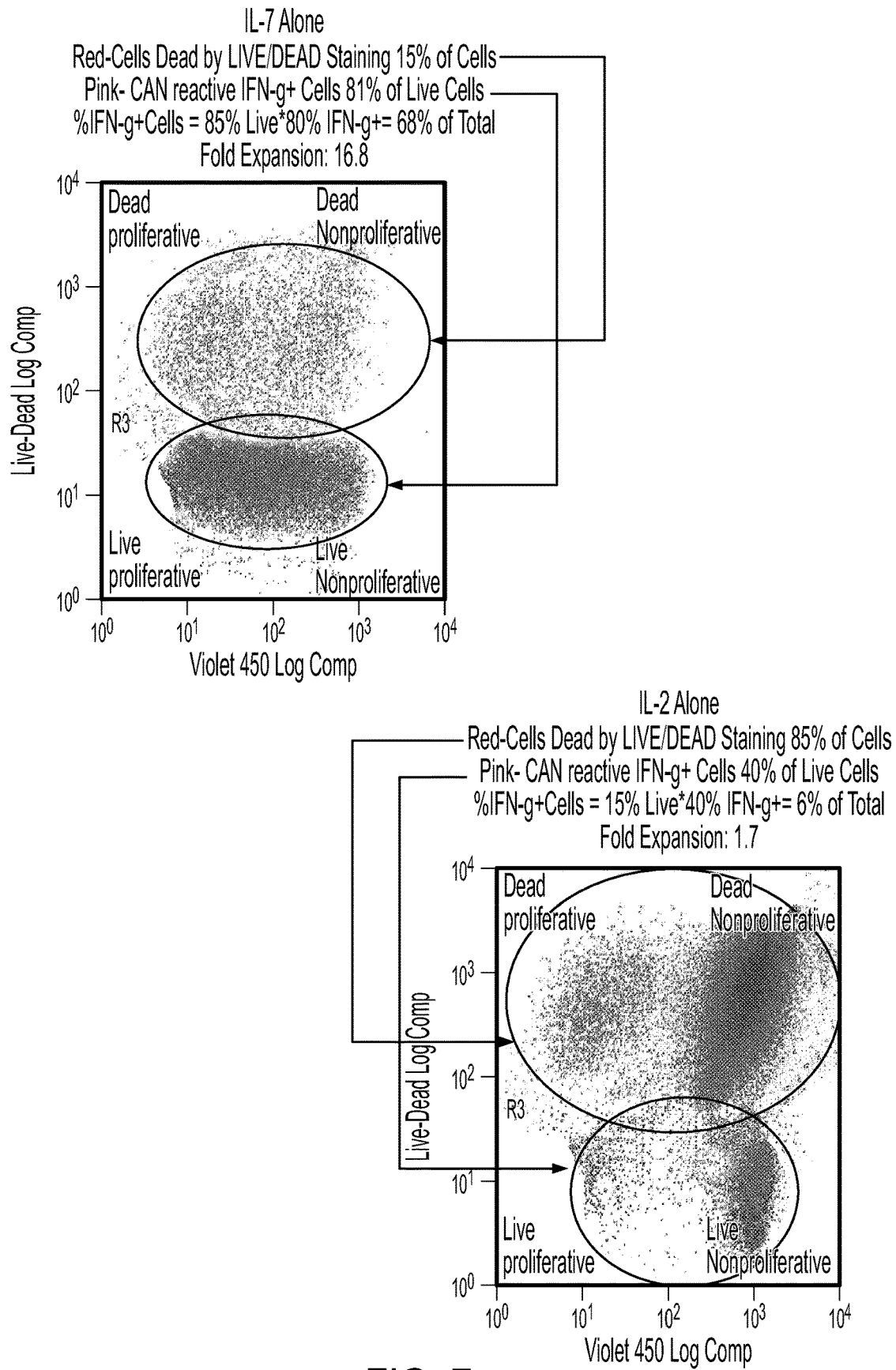
FIG. 7. Impact of rIL-7 vs rIL-2 on proliferation of Ag-specific T-cells in culture. CAN was the driving Ag; all groups received GM-CSF/resiquimod/LPS, then either rIL7 or IL2. Cultures were restimulated at end of 2nd week with freshly thawed autologous PBMC pulsed with CAN. Only CAN-specific T-cells making IFN-γ are shown. Cells were previously loaded with Cell Trace violet to gauge proliferation (X-axis shows violet intensity. A shift from right to left indicates greater proliferation as the violet dye dilutes in half every time a labelled T-cell divides. Cells also were exposed to a live-dead stain. Y-axis shows live-dead stain intensity (up is dead, down is live). CAN-specific T-cells in IL-7 proliferated more with many less dead cells and higher yields (e.g., "IL-7 group" 10.8 fold gross expansion, frequency of viable CAN-specific T-cells 81% at end of culture versus "IL-2 group" 1.7 fold gross expansion, frequency of viable CAN-specific T-cells 40% at end of culture, (10.8× 0.81)/(1.7×0.40) equals 12.9 fold higher number of CAN-specific T-cells present in "IL-7 group").

T-cells grown in IL-2 rather than IL-7 mostly died. Surviving Ag-specific T-cells released IFN-γ, but displayed minimum proliferation. In contrast, T-cells grown in IL-7 mostly survived and proliferated if they were Ag-specific, explaining the logarithmic greater yield and higher frequency of Ag-specific T-cells, both CD4+ and CD8+, in IL-7 based cultures (FIG. 7).

Figure 8:
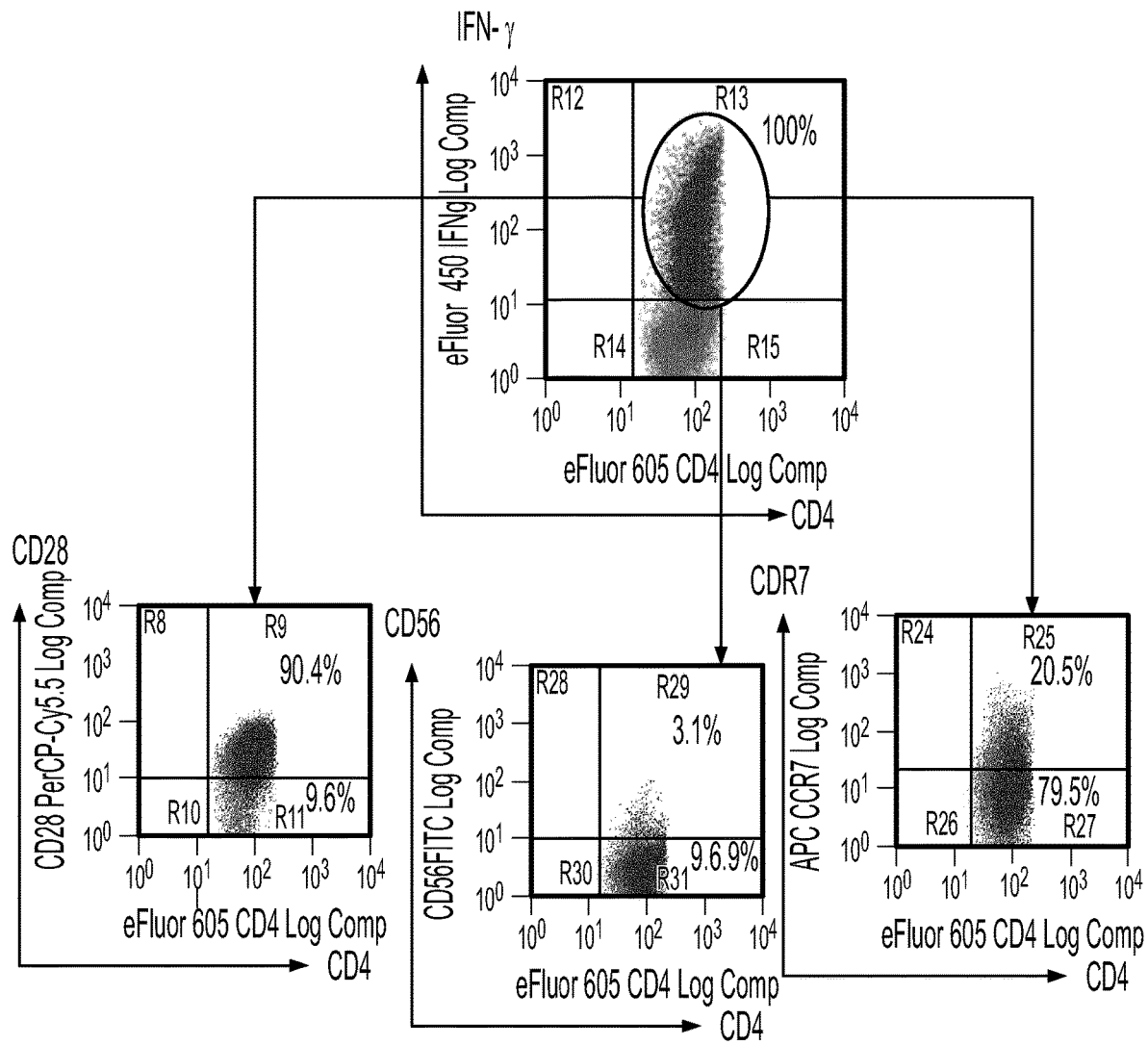
FIG. 8. Phenotype of 2 week cultured PBMCs employing "GM+TLR" culture method. Cells were pulsed day 1 with CAN. Upper dot plot shows ICC IFN-γ response 2 weeks later to fresh CAN-pulsed PBMC. Blue spike includes 100% of CAN-specific IFN-γ production by primed/expanded CD4$^+$ cells (39.5% of total CD4$^+$ T-cells showed CAN-specificity). Lower graphs show the expression of the blue spike CD4$^+$ cells of CD28, CD56, and CCR7. % in RUQ and RLQ show percentage of CD4/INF-γ$^+$ cells.
Figure 9:
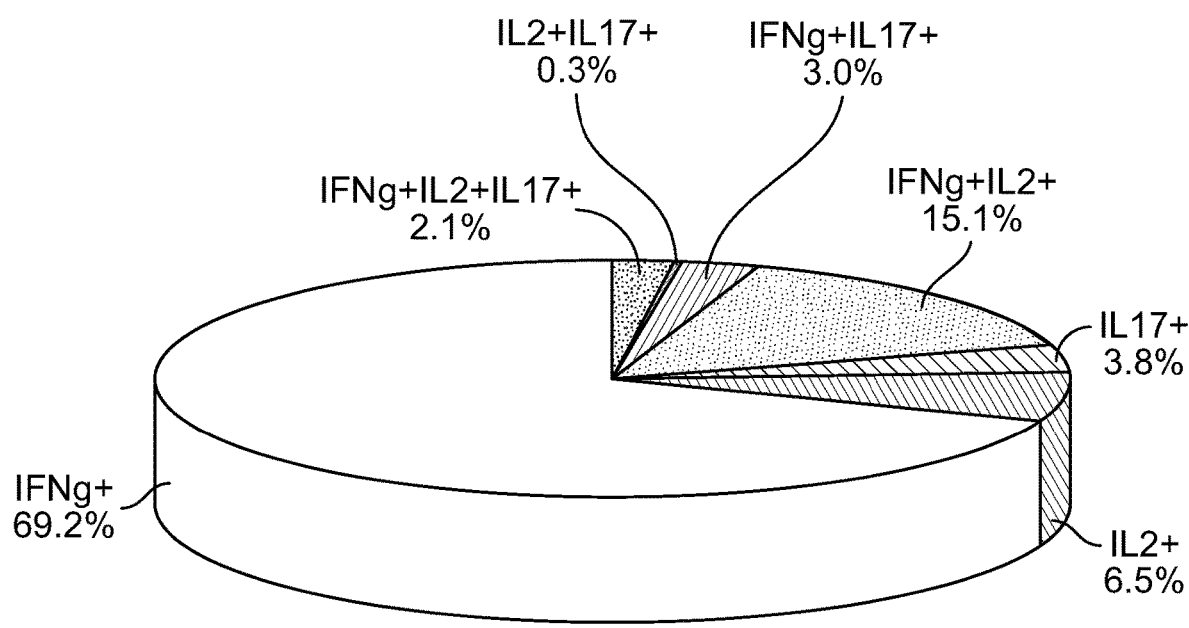
FIG. 9. A range of cytokine production can be evoked from the culture system. The pie graph shows that approximately 80% of CD4$^+$ T-cells secreted IFN-γ, IL-2, and/or IL-17 upon exposure to relevant Ag. Slices show % of Ag-specific T-cells that made either IFN-γ, IL-2, or IL-17; or combinations of two; or all three. These results demonstrate a "default" pattern of cytokine production straddling T1-*T17 functional phenotype. This distribution can indicate a highly effective population for adoptive immunotherapy.

The phenotype of the propagated Ag-specific T-cells in GM+TLR cultures was CD28+ and CD56−, a likely ideal state of "young" differentiation for adoptive T cell therapy (FIG. 8). Both CCR7$^{low}$ and CCR7$^{high}$ subpopulations were present, consistent with a mixed presence of memory effector and central memory subsets (FIG. 8).

Figure 10:
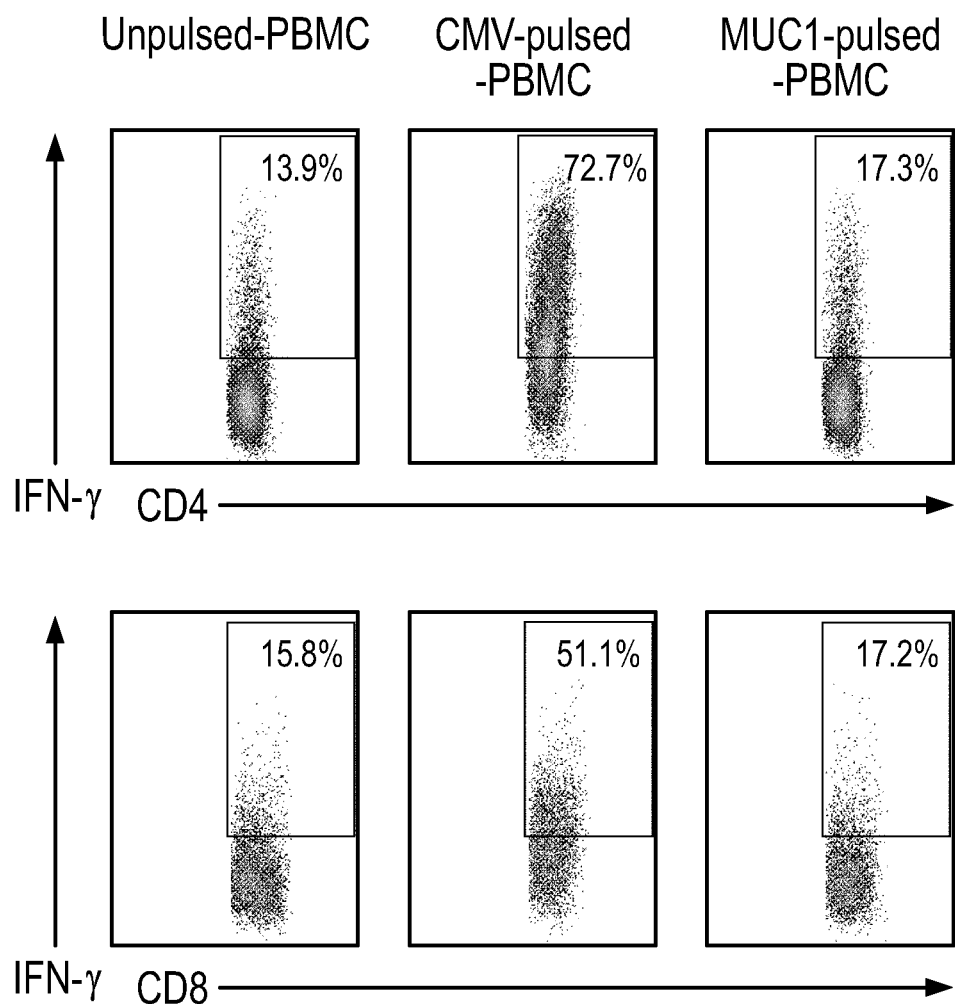
FIG. 10-12 are acquisition dot plots that are representative of the ability to selectively expand antigen-specific T-cells (both CD4$^+$ and CD8$^+$ T-cells) when cultures are driven by a CMV (cytomegalovirus) peptide (FIG. 10), a MUC1-derived peptide (FIG. 11), or a HER2/neu derived peptide (FIG. 12). In all cases, PBMCs were exposed to GM-CSF on Day 1 of culture, to the peptide antigen, then resiquimod, then LPS on Day 2 of culture, then to IL-7 beginning on Day 3. Polyclonal anti-CD3 stimulation was not performed. End of culture ranged from Day 12 to Day 21. Each figure shows the frequency of CD4$^+$ and CD8$^+$ T-cells making interferon-gamma upon re-exposure to the driving antigen or to control antigens at the end of culture (boxes within each dot plot show % of T-cells making interferon).
Figure 11:
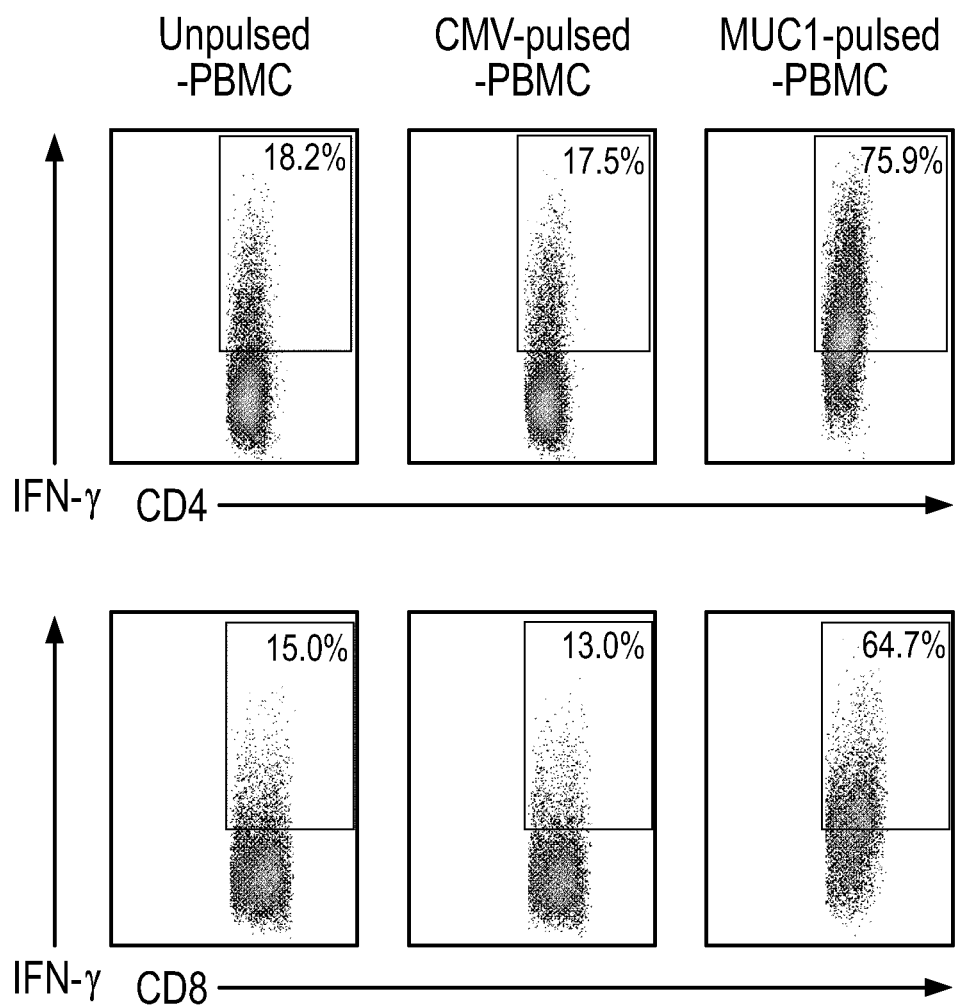
Figure 12:
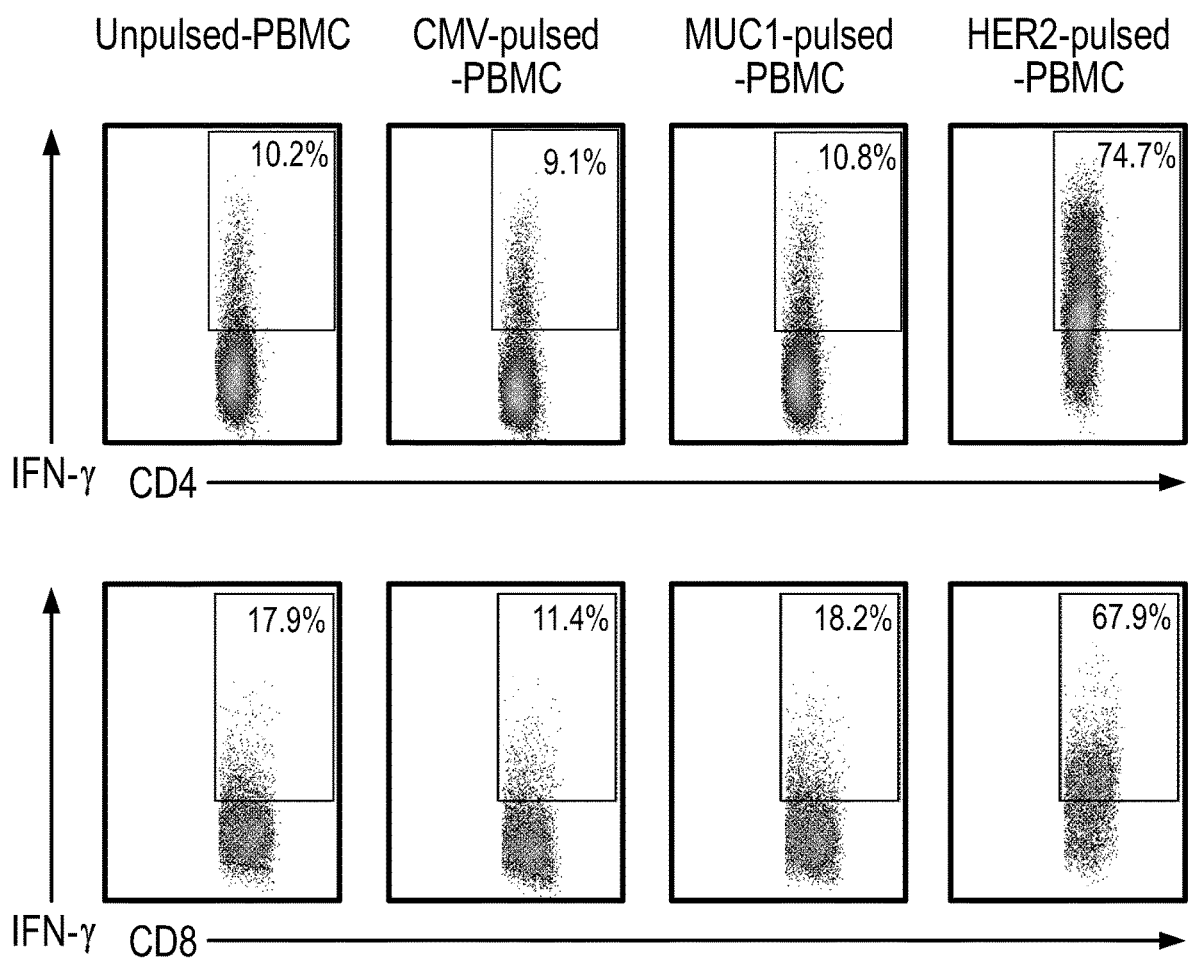
Figure 13:
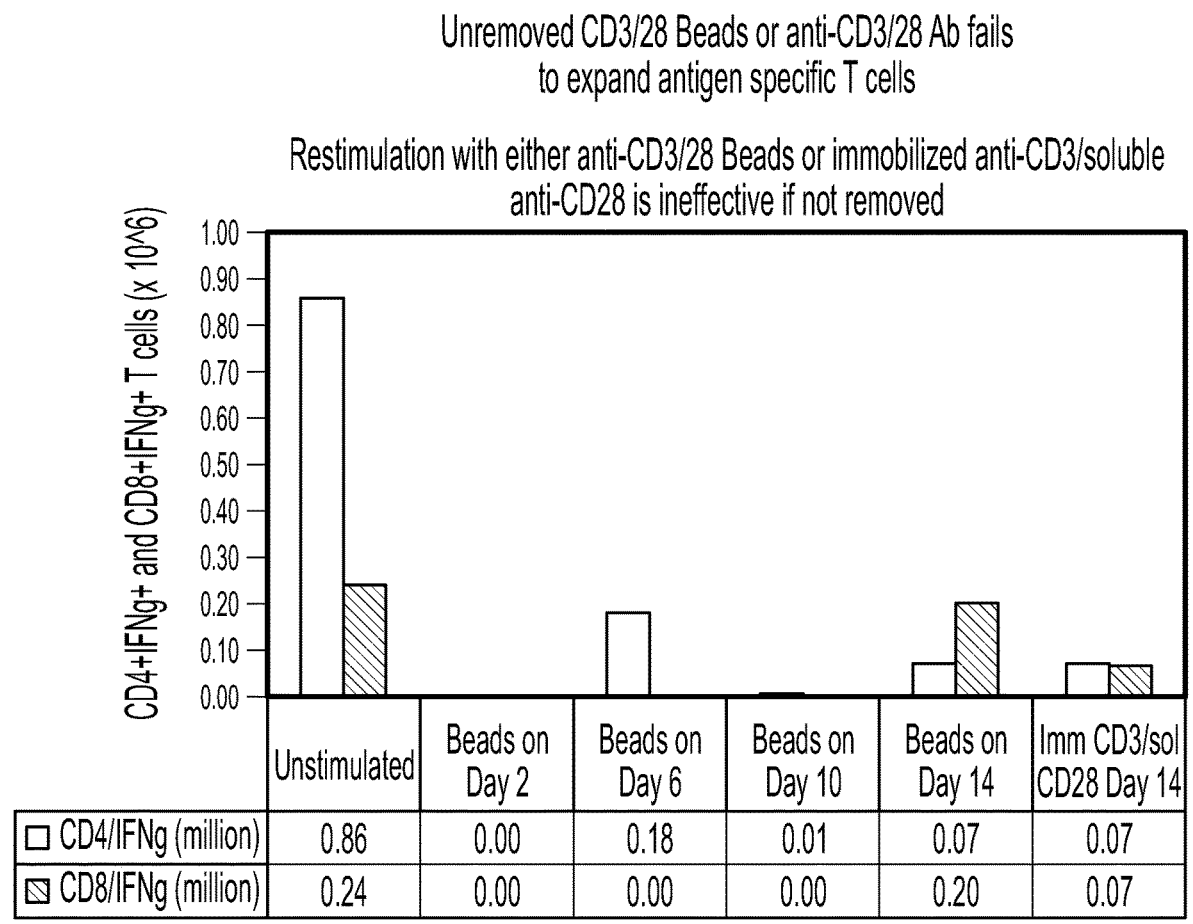
FIG. 13 is a graph showing that unremoved (a) anti-CD3 antibody/anti-CD28 antibody beads or (b) immobilized anti-CD3 antibody and soluble anti-CD28 antibody treatment failed to expand antigen-specific T cells. All groups stimulated with CMV peptide on Day 2 (Step 1). "Unstimulated" group received standard treatment only (GM-CSF day 1, R848+LPS+CMV peptide day 2, then expanded in IL7 to day 21). Other groups also received either Activator anti CD3/28 Dynabeads ("Beads") at 1:1 ratio or immobilized anti-CD3/soluble anti-CD28 ("Imm CD3/sol CD28") each at 1 μg/mL. Number of Ag-specific CD4 and CD8 T cells at Day 19 harvest calculated per million starting PBMC. Calculation=Fold Expansion×% CD4 or % CD8×producing % IFN-γ upon specific re-exposure to CMV peptide.
Figure 14:
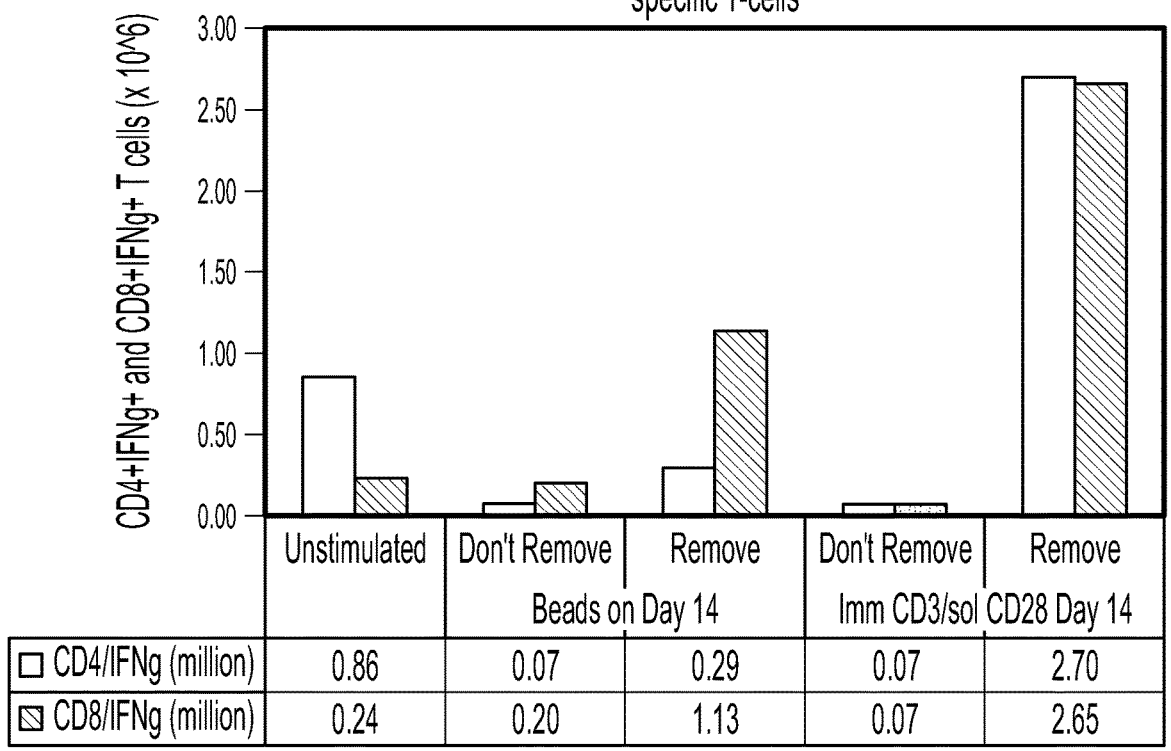
FIG. 14 is a graph showing that removing anti-CD3 antibody/anti-CD28 antibody beads or immobilized anti-CD3 antibody and soluble anti-CD28 antibody treatment allowed expansion of antigen-specific T cells. All groups stimulated with CMV peptide on Day 2 (Step 1). "Unstimulated" group as in FIG. 13. Other groups also received either Activator anti CD3/28 Dynabeads at 1:1 ratio or imm-CD3/sol-28 each at 1 μg/mL. Removal of beads and imm-CD3/sol-28 occurred 48 hours after addition. Number of Ag-specific CD4 and CD8 T cells at Day 21 harvest calculated as in FIG. 13.
Figure 15:
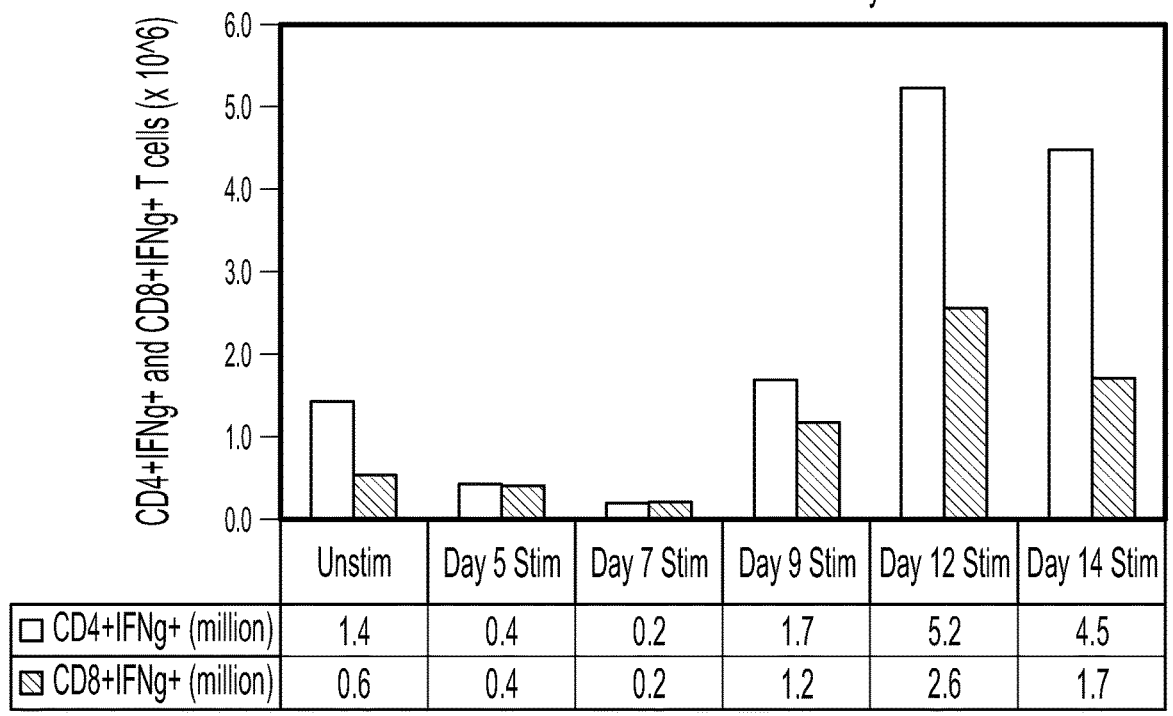
FIG. 15 is a graph showing results from restimulation of CMV-specific T cells with immobilized anti-CD3 antibody and soluble anti-CD28 antibody treatment on the indicated days. All groups stimulated with CMV peptide on Day 2 (Step 1). "Unstimulated" group as in FIG. 13. Other groups also received imm-CD3/sol-28 each at 1 μg/mL. Removal of imm-CD3/sol-28 occurred 48 hours after addition. Number of Ag-specific CD4 and CD8 T cells at Day 21 harvest calculated as in FIG. 13.
Figure 16:
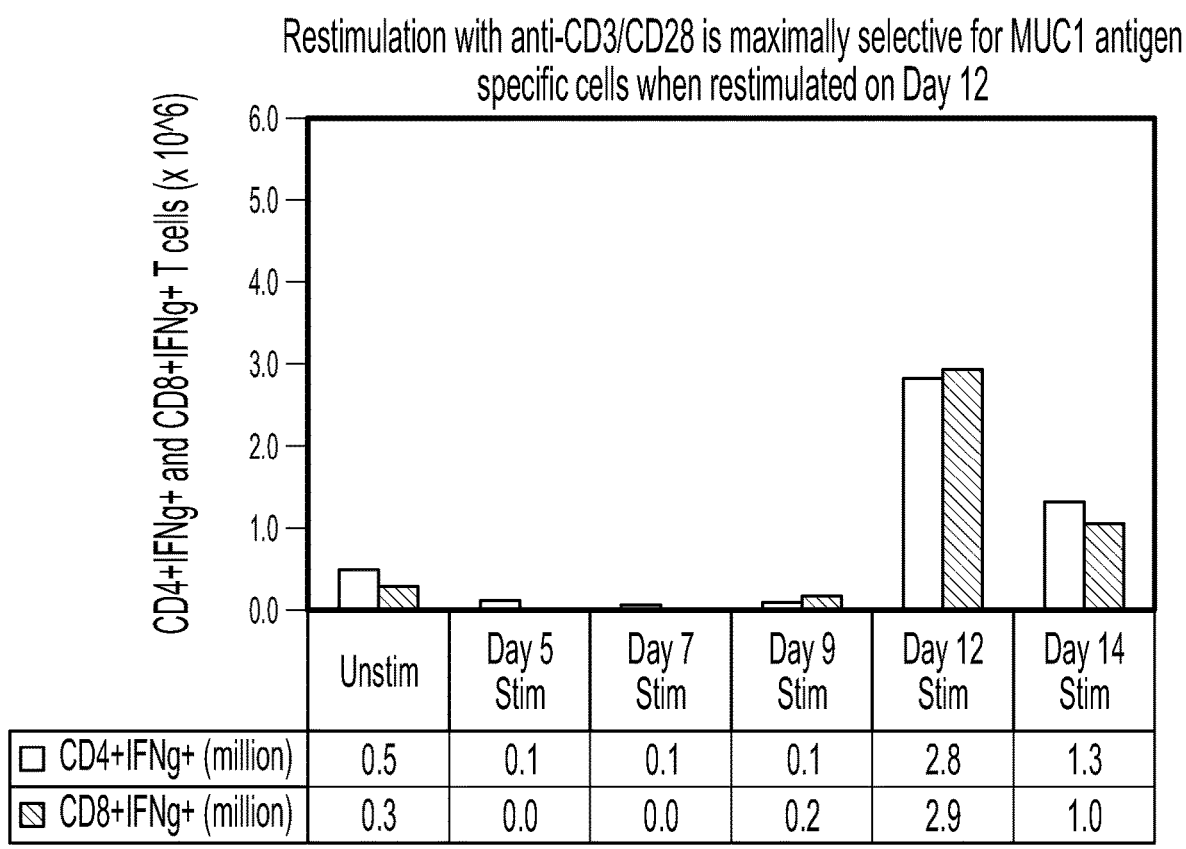
FIG. 16 is a graph showing results from restimulation of MUC1-specific T cells with immobilized anti-CD3 antibody and soluble anti-CD28 antibody treatment on the indicated days. All groups stimulated with MUC1 peptide on Day 2 (Step 1). "Unstimulated" group received standard treatment only (GM-CSF day 1, R848+LPS+MUC1 peptide day 2, then expanded in IL7 to day 21). Other groups also received imm-CD3/sol-28 each at 1 μg/mL. Removal of imm-CD3/sol-28 occurred 48 hours after addition. Number of Ag-specific CD4 and CD8 T cells at Day 21 harvest calculated as in FIG. 13.
Figure 17:
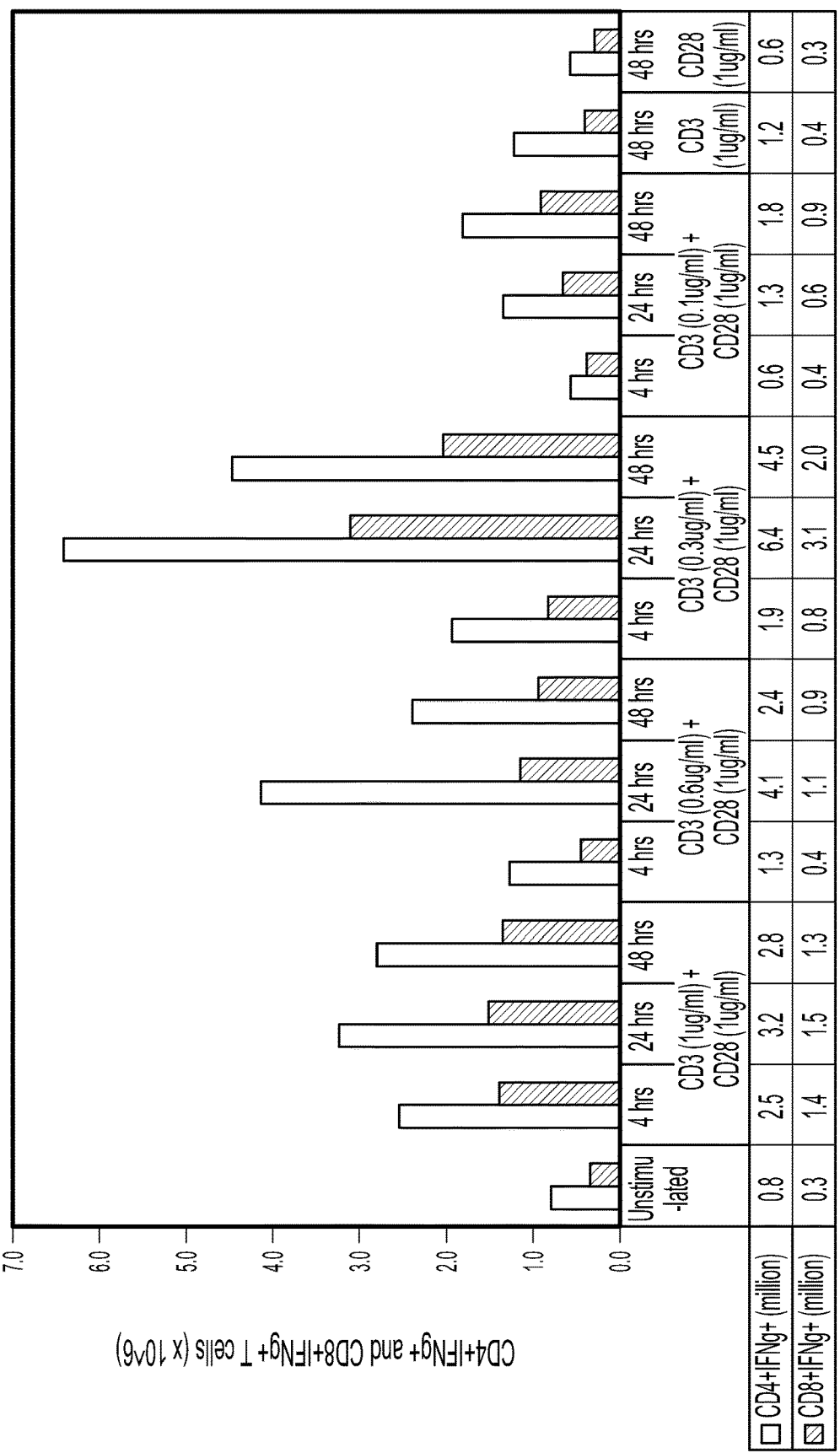
FIG. 17 is a graph showing cell expansion results from restimulation of MUC1-specific T cells with an immobilized anti-CD3 antibody treatment, a soluble anti-CD28 antibody treatment, an immobilized anti-CD3 antibody and soluble anti-CD28 antibody treatment at the indicated doses for the indicated times. The methods were the same as for FIG. 16.
Figure 18:
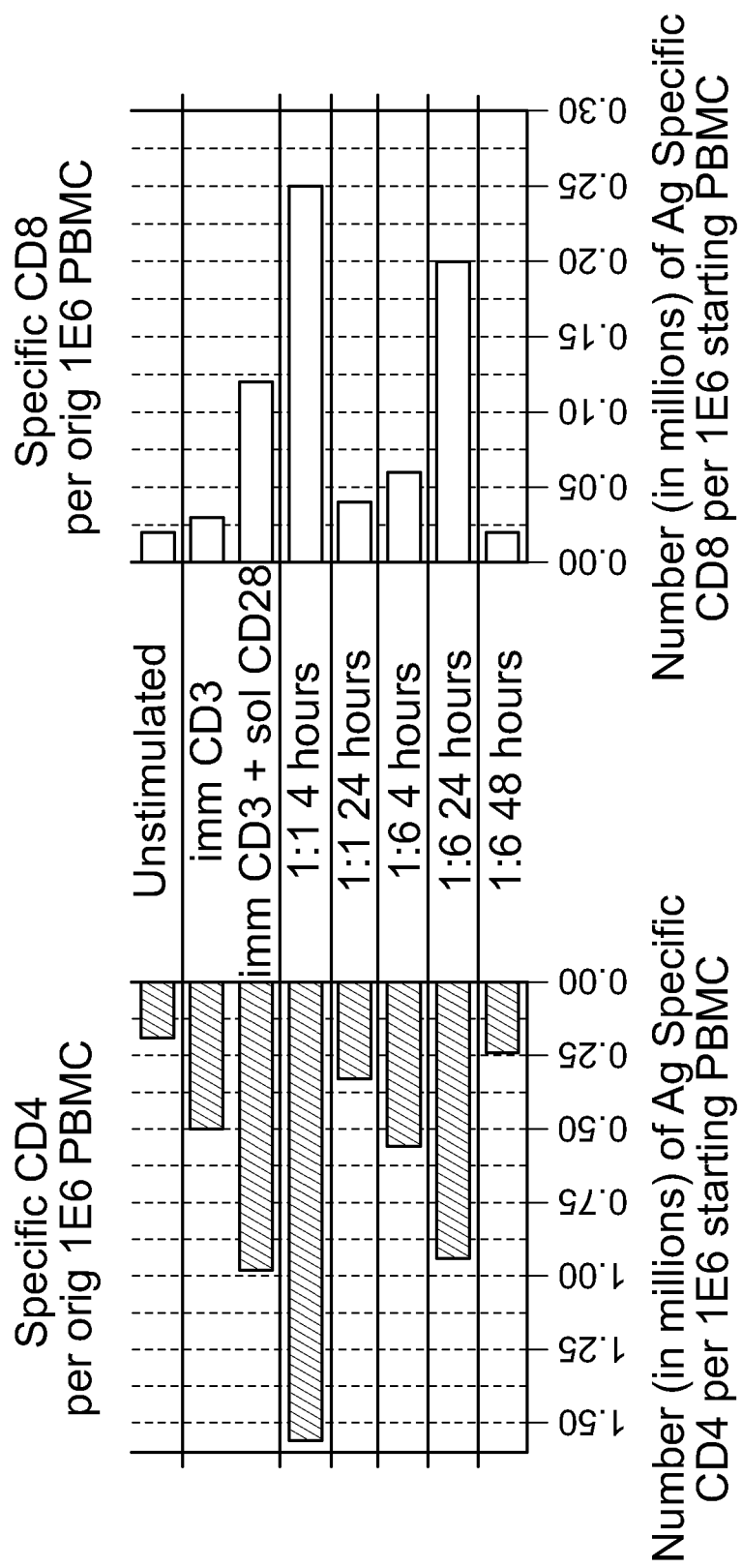
FIG. 18 is a graph showing cell expansion results from restimulation of MUC1-specific T cells with anti-CD3 antibody/anti-CD28 antibody beads or an immobilized anti-CD3 antibody and soluble anti-CD28 antibody treatment at the indicated ratios for the indicated times. All groups received MUC1 peptide Day 2. "Unstimulated" group as in FIG. 13. Imm-CD3 used at concentration of 0.3 μg/mL. Soluble CD28 used at concentration of 1.0 μg/mL. Activator Dynabeads are used at bead to T-cell ratio and for bead exposure duration shown. Number of Ag-specific CD4 and CD8 T cells at Day 21 harvest calculated as in FIG. 13.

FIG. 10-12 are acquisition dot plots that demonstrate the ability to selectively expand antigen-specific T-cells (both CD4+ and CD8+ T-cells) when cultures are driven by a CMV (cytomegalovirus) peptide (FIG. 10), a MUC1-derived peptide (FIG. 11), or a HER2/neu derived peptide (FIG. 12). In all cases, PBMCs were exposed to GM-CSF on Day 1 of culture, to the peptide antigen, then resiquimod, then LPS on Day 2 of culture, then to IL-7 beginning on Day 3. The end of culture ranged from Day 12 to Day 21. No polyclonal stimulation step was performed. Each figure shows the frequency of CD4+ and CD8+ T-cells making interferon-gamma upon re-exposure to the driving antigen or to control antigens at the end of culture (boxes within each dot plot show % of T-cells making interferon-gamma). These figures demonstrate the ability of GM-CSF, resiquimod, LPS, and interleukin-7 to generate rapid enrichment of Ag-specific CD4+ and CD8+ T cells even without polyclonal anti-CD3 stimulation. FIGS. 13-18 demonstrate how anti-CD3 polyclonal stimulation of defined optimal duration, followed by further culture in the absence of polyclonal stimulation, can substantially increase both the absolute yields and often the frequency of antigen-specific T-cells.

Taken together, these results demonstrate that large numbers of antigen-specific T cells can be achieved from PBMCs within 21 days or less.

Example 2—Generating Populations of Antigen-Specific T Cells from PBMCs

The following was performed to confirm that PBMCs from patients with advanced breast cancer can be expanded as described herein (with the exception of the anti-CD3 bead stimulation at Day 12 of culture) to generate both CD4$^+$ and CD8$^+$ natural T-cells that recognize cancer-associated antigens such as MUC1 and/or HER2. The following also was performed to confirm that T cells can be successfully sensitized even when the antigens are provided as cocktails of polypeptides, rather than as individual polypeptides.

Briefly, PBMCs were obtained from a 42 year old female patient diagnosed with right-sided ER−/PR−/HER2+ breast cancer, treated initially with neoadjuvant chemotherapy including Herceptin (trastuzumab) and surgical resection, and placed on maintenance Herceptin. Liver metastasis was identified, and she started receiving ado-trastuzumab emtansine (Kadcyla). After four cycles, brain metastasis became apparent for which she received stereotactic radiation therapy. PBMCs were collected and cryopreserved prior to further dosing with Kadcyla. Thawed PBMCs were cultured as described herein, exposing the PBMCs on Day 2 to a cocktail of MUC1-derived peptides (SEA1, SEA2, and SEA3), with or without a control CMV-derived peptide also added to the cocktail (each peptide at 10 g/mL). After culture expansion in interleukin-7 to day 19 of culture, T-cells were re-exposed to freshly thawed autologous PBMCs pulsed with individual relevant and control peptides.

Figure 19:
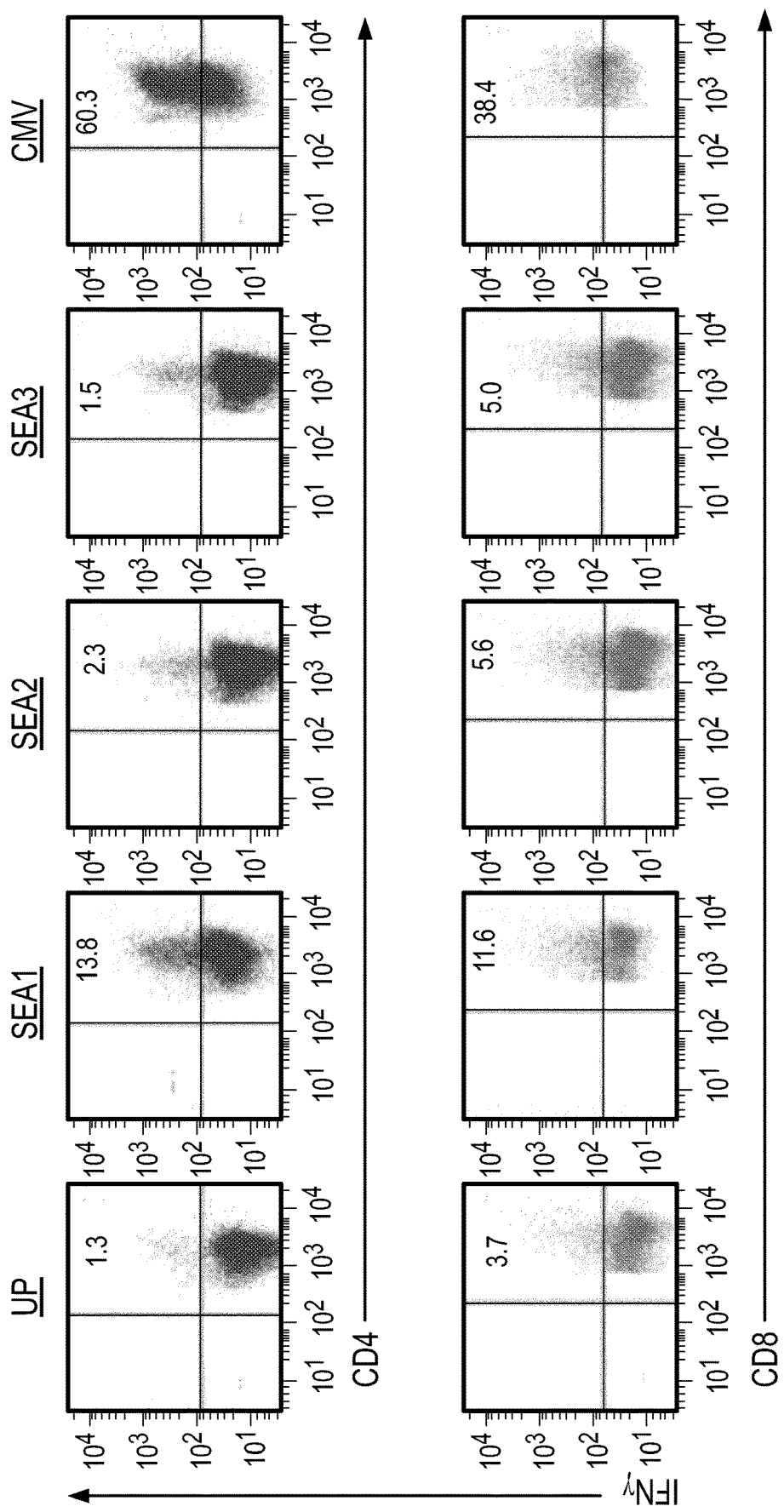
FIG. 19. PBMCs from patients with advanced breast cancer can be expanded as described herein to generate both CD4$^+$ and CD8$^+$ natural T-cells that recognize cancer-associated antigens such as MUC1 and/or HER2. Culture outcome for PBMC assayed on Day 19, from patient with advanced breast cancer exposed on culture day 2 to a cocktail of SEA1, SEA2, SEA3, and CMV polypeptides. Plots show % of CD4$^+$ or CD8$^+$ T-cells producing IFNγ at culture end when restimulated with freshly thawed autologous PBMC either unpulsed (UP) or pulsed with individual peptides.

Results were obtained on Day 19 of culture when the Day 2 cocktail contained both SEA (MUC1-derived) peptides and cytomegalovirus (CMV) peptide, demonstrating that both CD4$^+$ and CD8$^+$ T-cells derived by the culture method were highly enriched for recognition of at least a portion of the driving antigens, in this case both CMV and SEA1 specificities (FIG. 19). In contrast, T-cells sensitized to a cocktail of MUC1-derived peptides not including CMV recognized MUC1 peptides at culture's end, but not CMV (not shown). Generated MUC1-specific T-cells can be therapeutically active if reinjected as autologous adoptive immunotherapy into patients with MUC1-expressing malignancies, which include the great majority of patients with breast, pancreatic, colorectal, and many other cancer types. Because the patient PBMCs in this example were limited in number (obtained by peripheral phlebotomy rather than leukapheresis), the experiment was run as a small scale screening culture in 24 well plates. The anti-CD3/CD28 culture stimulation step was omitted but can be included. PBMCs from patients with additional types of advanced cancers can be used. Successful activation of MUC1-reactive and/or HER2neu-reactive T-cells using the culture system described herein was representative for three patients with advanced breast cancer and one patient with non-recurrent breast cancer.

Figure 20:
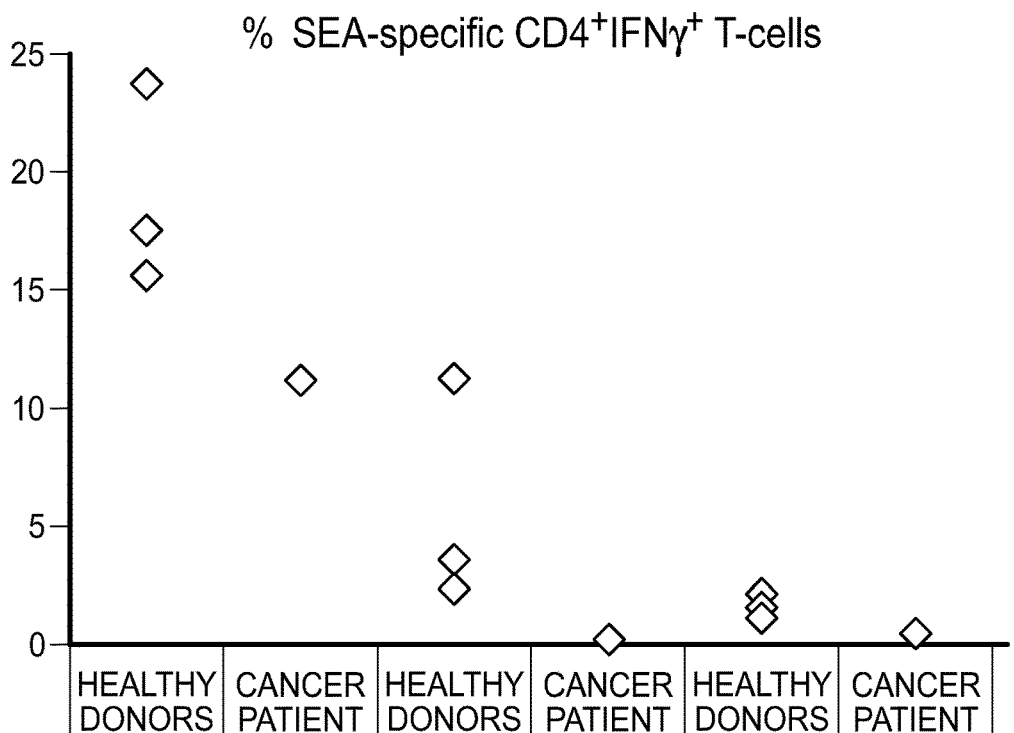
FIG. 20. Culture outcome for PBMC assayed on Day 19, comparing patient with advanced breast cancer with three healthy donors, each exposed on culture day 2 to a cocktail of MUC1-derived peptides (SEA1, SEA2, and SEA3).
Figure 20:
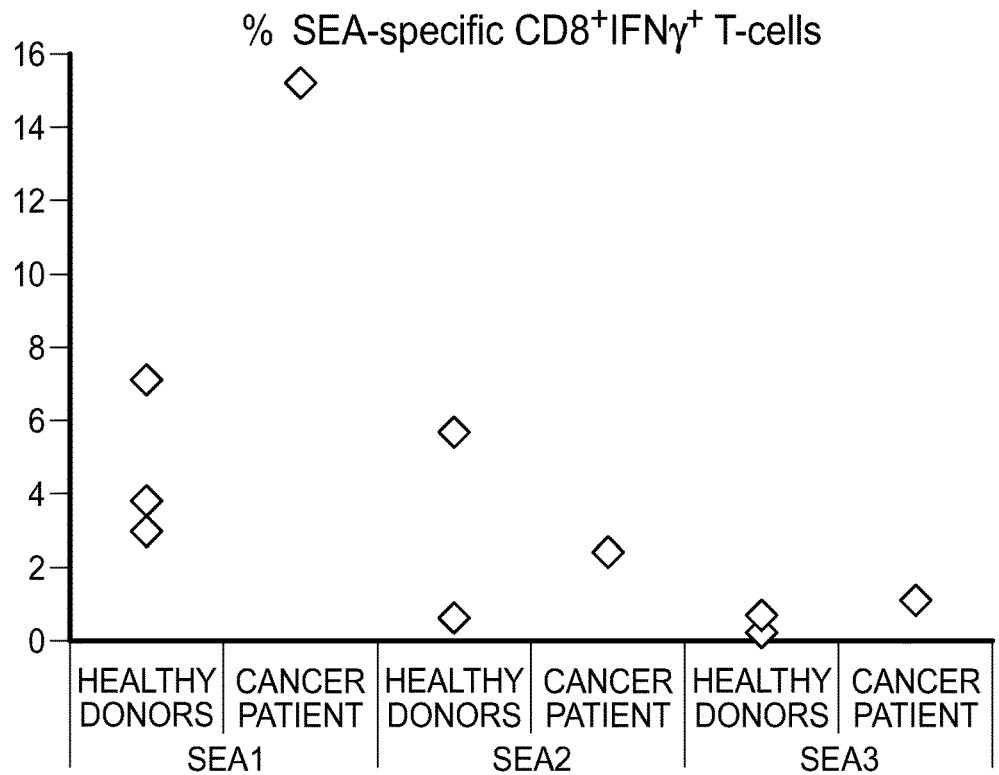

As evidenced in FIGS. 19 and 20, the culturing did not require that polypeptides be added individually to culture. Thawed PBMCs from leukapheresed healthy donors or cancer patients were cultured as described herein, exposing the PBMCs on Day 2 to polypeptide cocktails. Data show that the T-cells derived from the culture method were highly enriched by Day 19 for recognition of at least a subset of the driving antigens for both CD4$^+$ and CD8$^+$ cells. Interestingly, while individually pulsed polypeptides generated a maximal enrichment if pulsed at 50 μg/mL, cocktail pulsing worked better at 10 μg/mL for each polypeptide, meaning that cocktails allowed conservation of not only polypeptide, but also of PBMCs and every cell other culture reagent, since far less PBMCs were required to generate the same absolute number of Ag-reactive T-cells when cocktails were employed. Furthermore, the cocktail approach can allow the cultures to go forward for therapeutic administration even if different donors exhibit disparate T-cell sensitizations (for example, to SEA2 and/or SEA3 rather than (or in addition to) SEA1).

Figure 21:
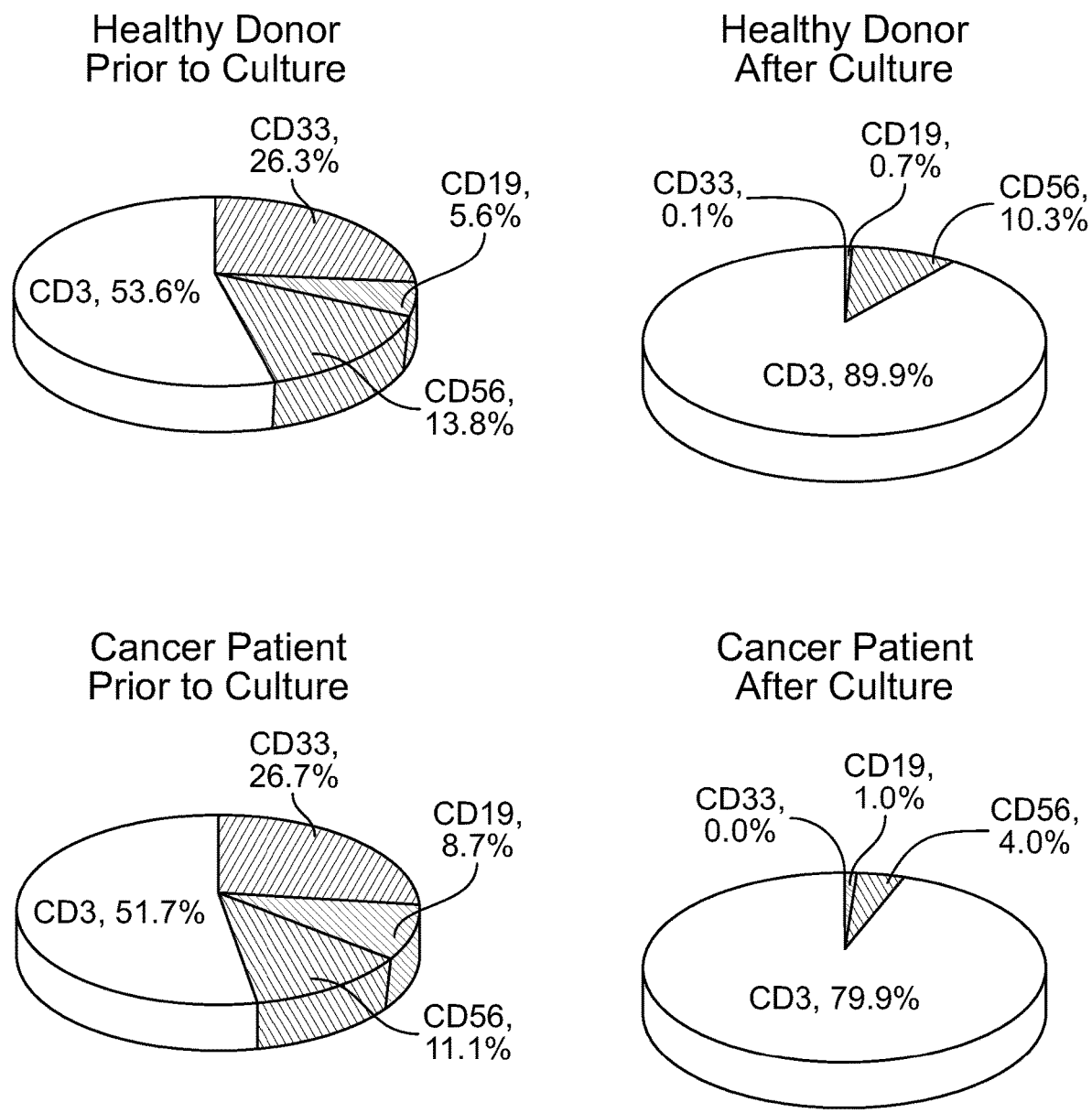
FIG. 21. CD3$^+$ T cells, CD19$^+$ B-cells, CD33$^+$ myeloid cells, and CD56$^+$ natural killer cells prior to and after culture.
Figure 22:
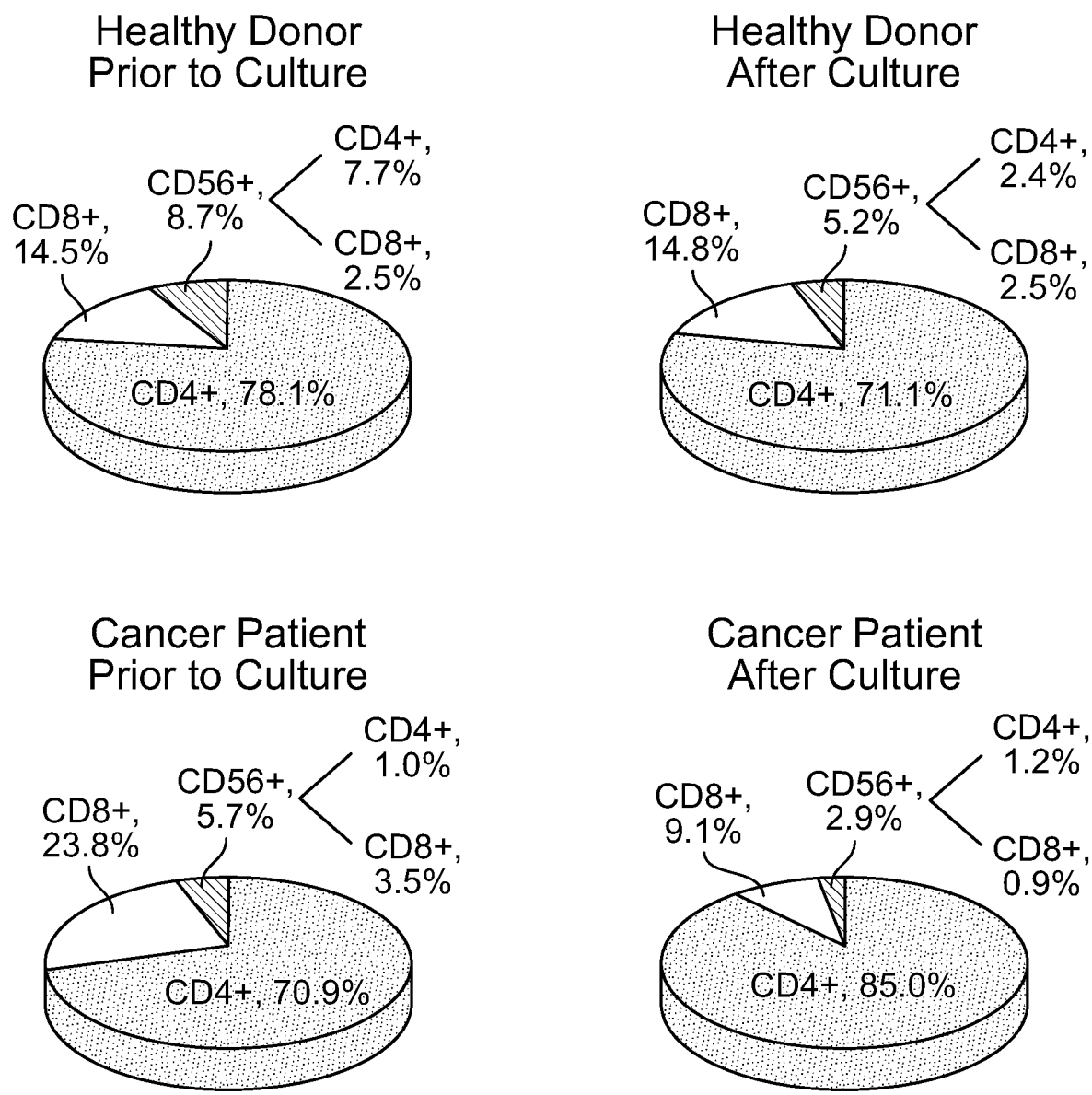
FIG. 22. CD3$^+$ (CD4$^+$, CD8$^+$, and CD56$^+$) T cells before and after culture.

FIGS. 21 and 22 show representative compositions of different cell lineages before and after culture from a representative healthy donor and a cancer patient. Before culture, T-cells (CD3$^+$) were around 50% of the total PBMC, with myeloid monocytes (CD33+), B-cells (CD19+), and NK cells (CD56$^+$) constituting the other lineages present (FIG. 21). At culture's end (Day 19), CD33$^+$ and CD19$^+$ cells were scant in number (FIG. 21), whereas CD3$^+$ T-cells represented 80-90% of total cells (FIG. 21). As shown in FIG. 22, CD4$^+$ T-cells continued to represent the majority of CD3$^+$ T-cells between Day 0 and 19, but CD8$^+$ T-cells also expanded (FIG. 22) and also were enriched for Ag-specific reactivity (FIGS. 19 and 20).

Whether from a healthy donor or a cancer patient, T-cells generated as described herein variably expressed CD28, PD1, CTLA4, and Foxp3 at the end of culture (Day 19). T-cells were analyzed for coexpression of various receptors for costimulatory ligands (CD28, the activating receptor for B7.1; CTLA4, the inhibitory receptor for B7.1; and PD1, the inhibitory receptor for PD-L1 (aka B7H1)).

Figure 23:
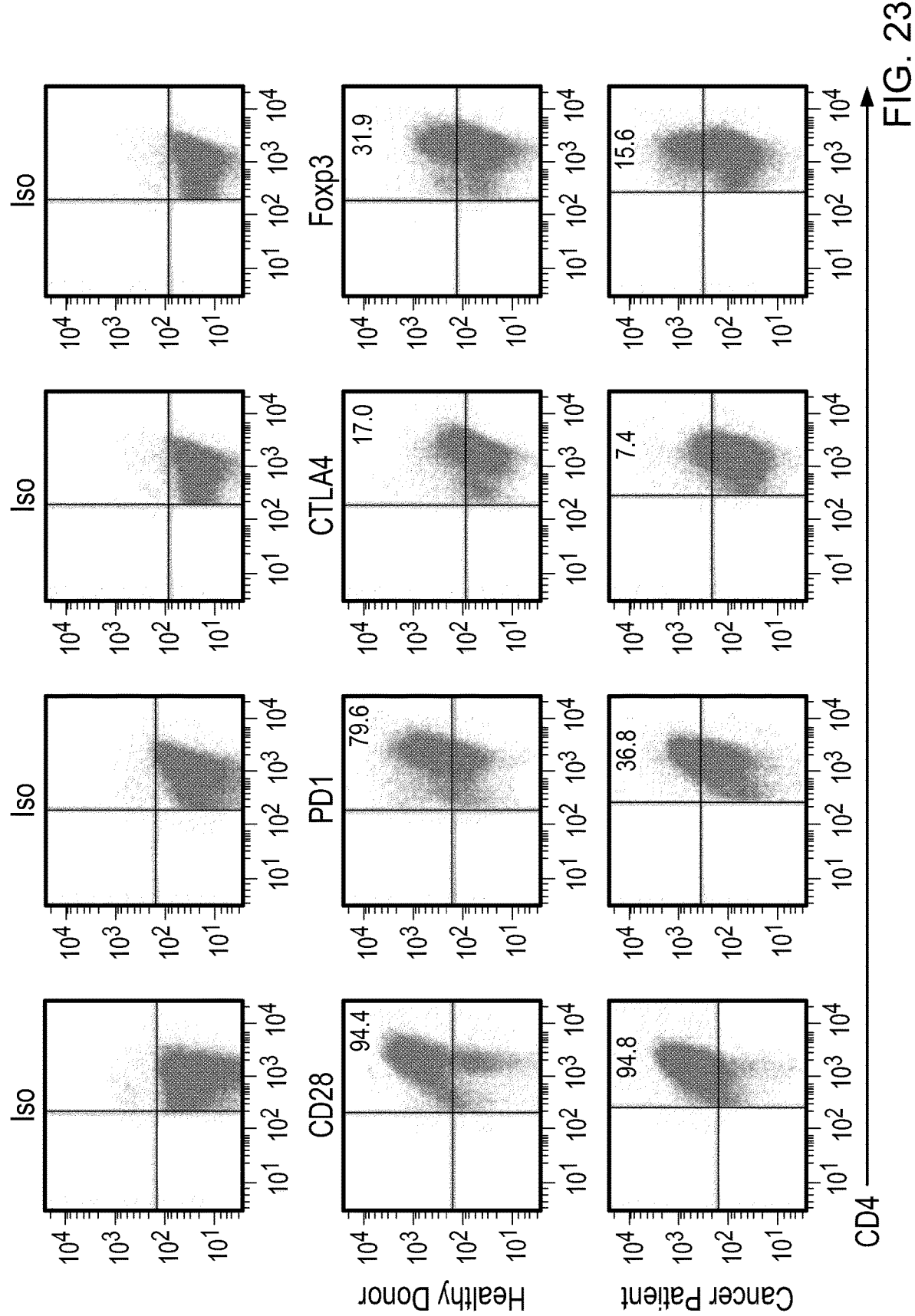
FIG. 23. Costimulatory receptor and Foxp3 expression on T-cells at end of culture.
Figure 23:
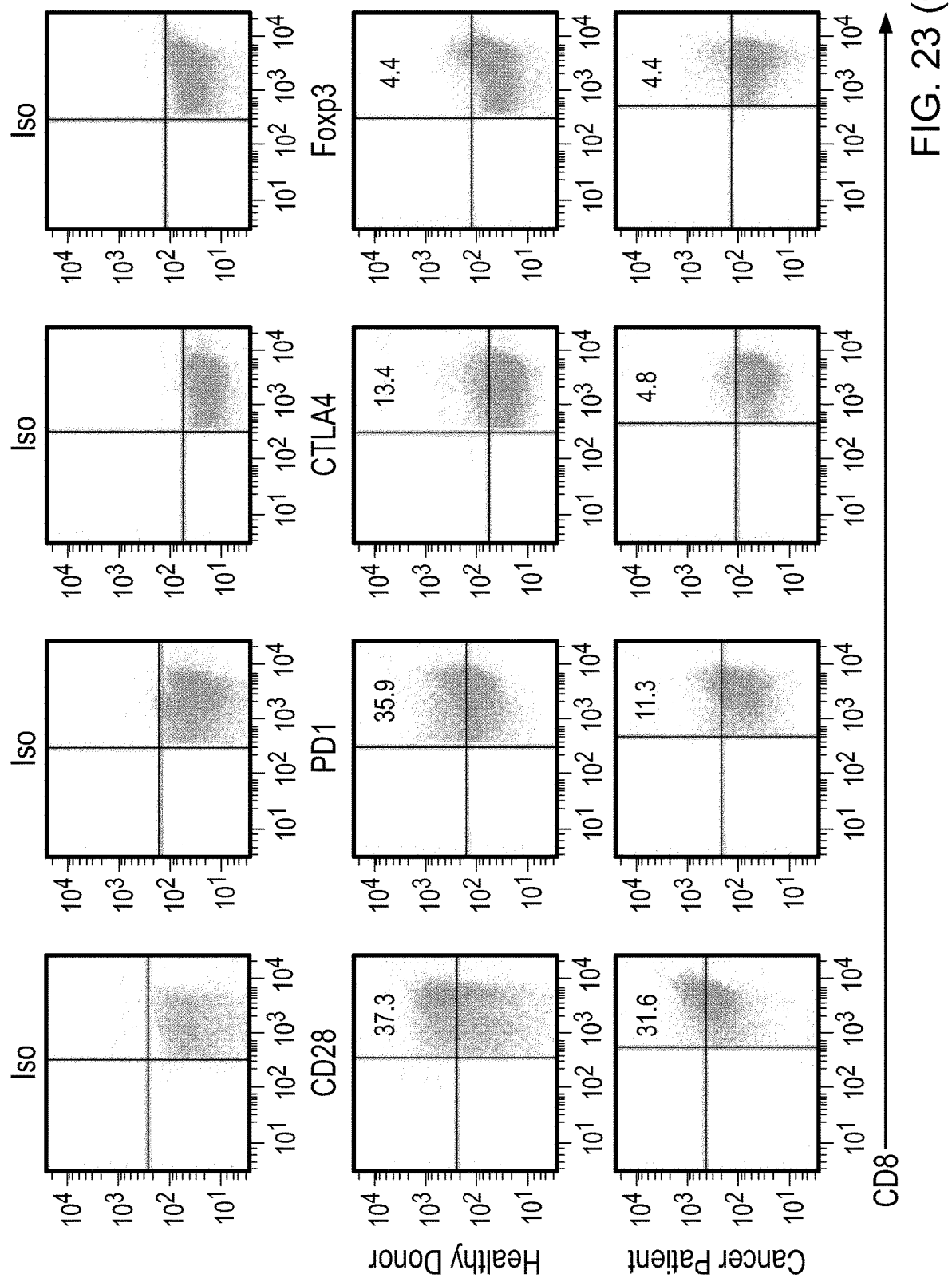
Figure 24:
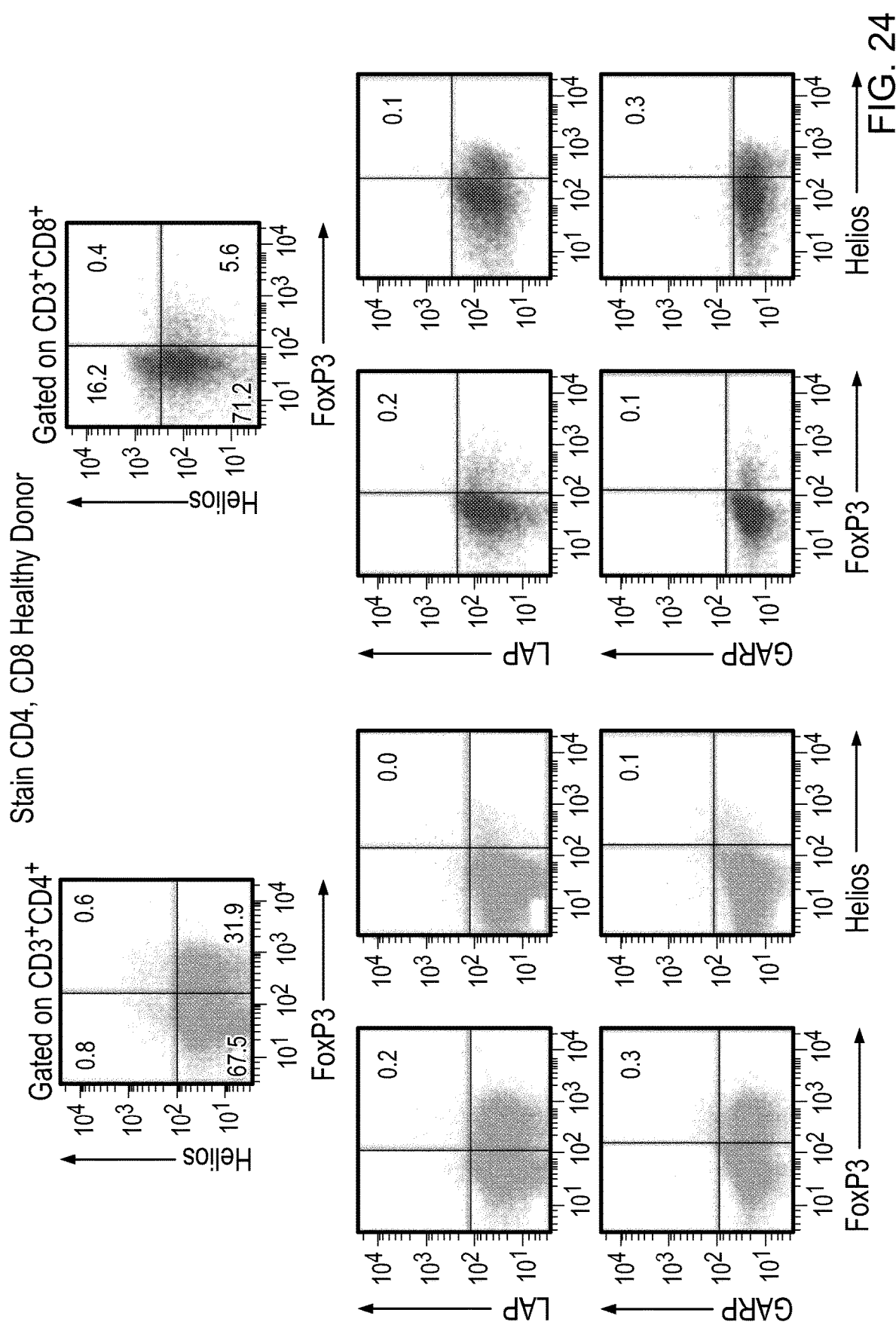
FIG. 24. Coexpression of LAP, GARP, and Helios on Foxp3$^+$ T-cells at end of culture.
Figure 24:
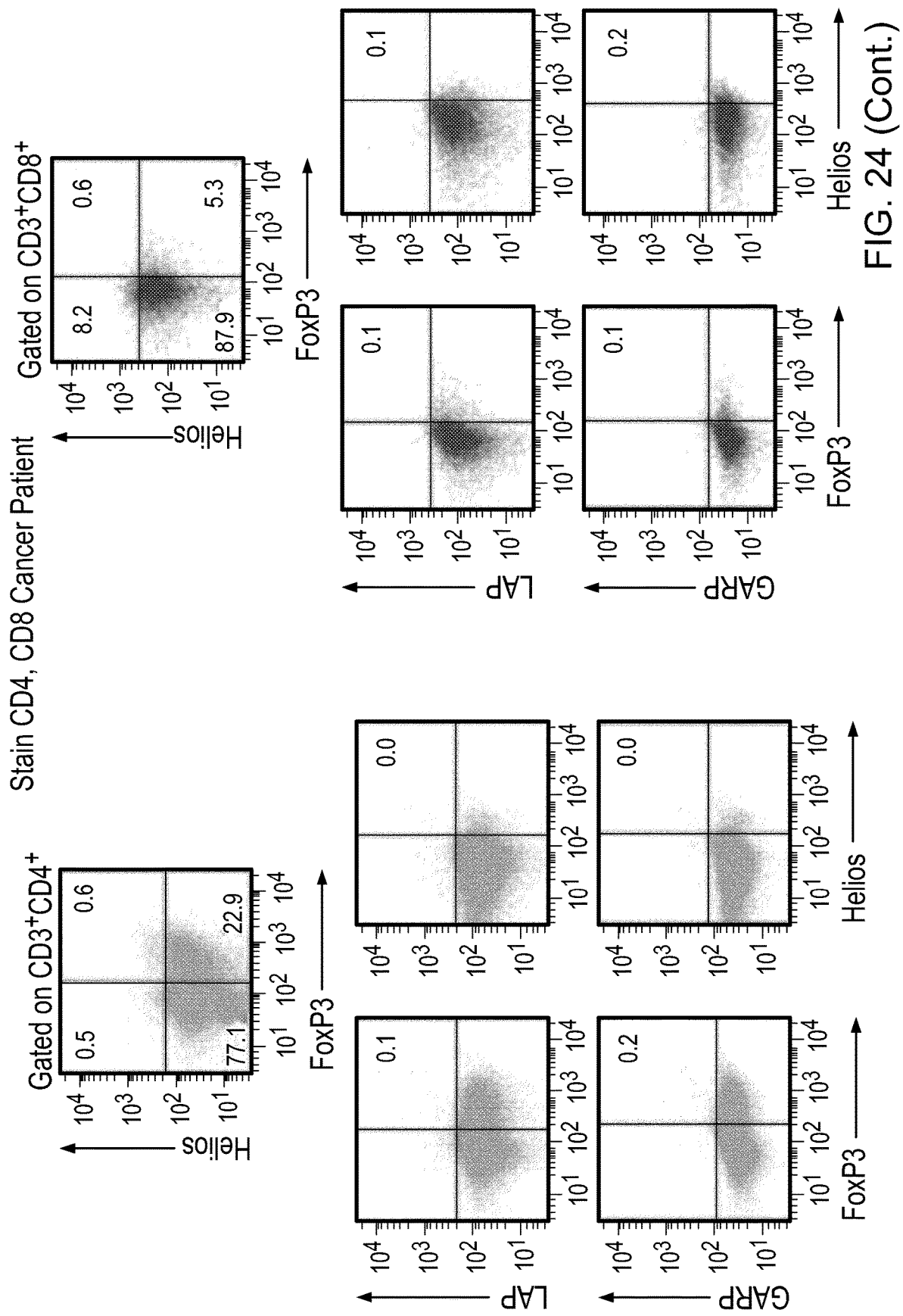

The percent of total CD4$^+$ or CD8$^+$ T-cells expressing these receptors and/or Foxp3 at Day 19 of culture was determined (FIG. 23). Representative isotype mAb staining (negative control) was shown in FIG. 23 as "Iso". Further, subanalysis in FIG. 24 of the Foxp3$^+$ subpopulation revealed that trivial numbers of the Foxp3$^+$ T-cells coexpress LAP or GARP, meaning that the great majority of Day 19 Foxp3$^+$ T-cells were effector rather than regulatory T-cells (FIG. 23). Similarly, the Helios$^+$ subpopulation expressed negligible levels of LAP or GARP (FIG. 23), meaning that the Helios$^+$ T-cell subset also constituted effector rather than regulatory T-cells. Furthermore, expression of PD1 and/or CTLA4 in FIG. 23 means that adoptive reinfusion of these T-cells may likely be therapeutically potentiated by checkpoint inhibitors that block PD1 (nivolumab and pembrolizumab) and/or CTLA4 (ipilimumab) (Topalian et al., *Nat. Rev. Cancer.*, 16(5):275-87 (2016)).

Figure 25:
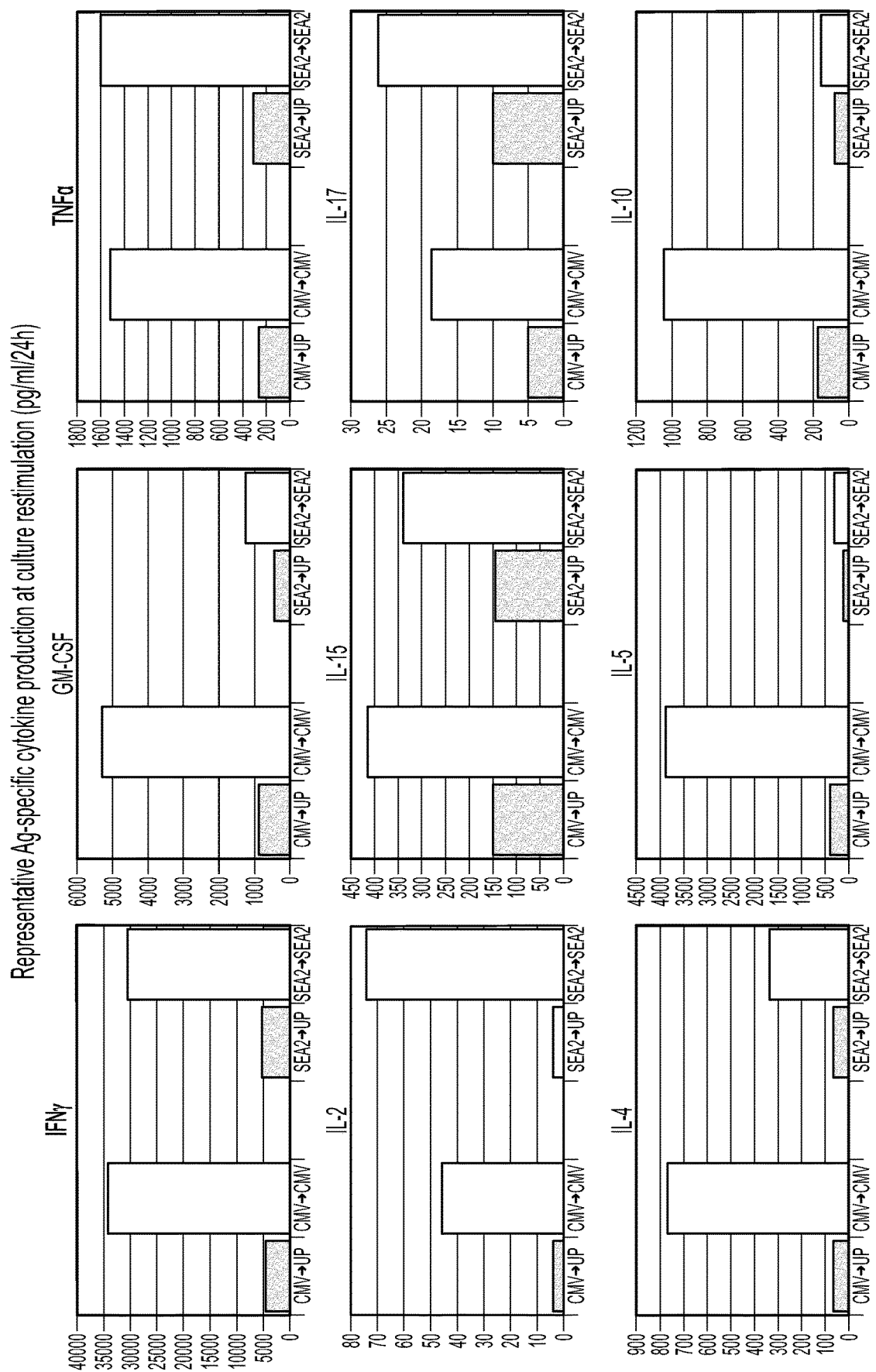
FIG. 25. Ag-specific cytokine production at end of culture.

Luminex assays at culture's end demonstrated that many cytokines were secreted by cultured T-cells upon re-exposure to the culture-driving Ag, dominated by, but not limited to, IFN-γ secretion (FIG. 25). CMV-driven cultures (first two bars of each graph of FIG. 25) were re-stimulated with freshly thawed autologous PBMC, either unpulsed (first bar of each graph of FIG. 25) or CMV-pulsed (second bar of each graph of FIG. 25). Similarly, SEA2-driven cultures (last two bars of each graph of FIG. 25) were re-stimulated with freshly thawed autologous PBMC, either unpulsed (third bar of each graph of FIG. 25) or SEA2-pulsed (fourth bar of each graph of FIG. 25). Such IFN-γ dominance may indicate that the therapeutic potency of T-cells expanded by these methods is high (Schwartzentruber et al., *J. Immunol.*, 146(10):3674-81 (1991)).

Figure 26:
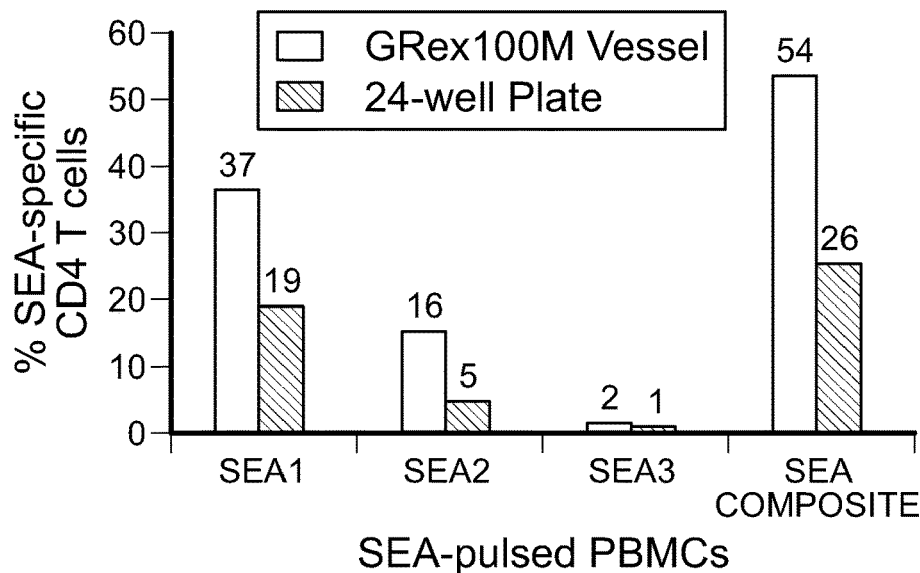
FIG. 26. T-cell culture expansion and Ag-specific frequency in 24 well plates vs Wilson-Wolf vessels.
Figure 26:
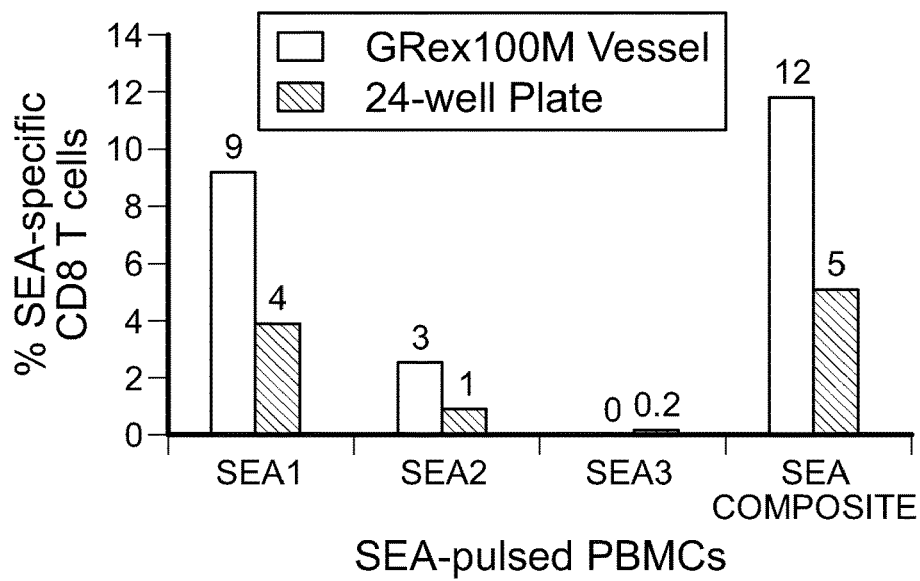
Figure 26:
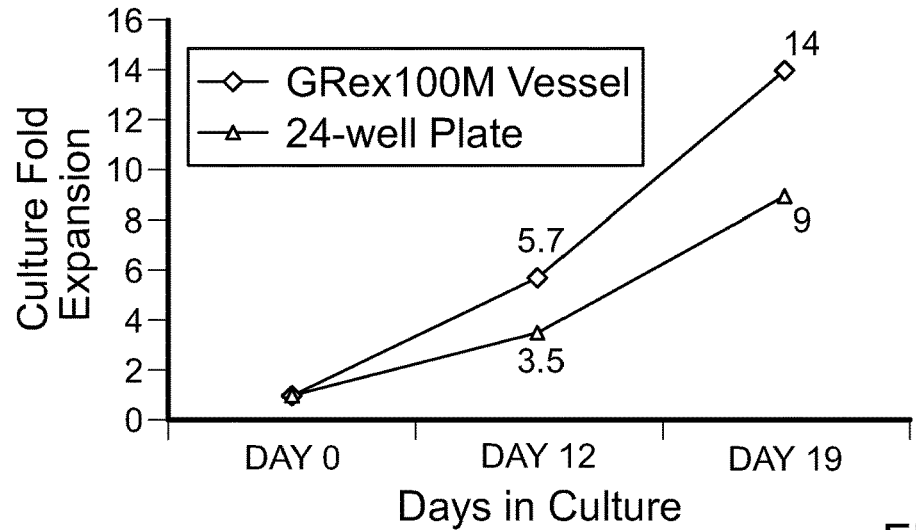

In addition, bulk expansion of Ag-driven PBMCs in Wilson-Wolf culture vessels worked better than small scaled cultures in 24 well plates (FIG. 26). Wilson-Wolf G-Rex vessels with gas-permeable "base" membranes were developed by Wilson-Wolf to prevent untoward acidity from building up in bulk T-cell cultures (Jin et al., *J. Immunother.*, 35(3):283-92 (2012)). This allowed a variety of large scale cultures to be sustained improved total T-cell yields and Ag-reactive frequency at 19 days of culture, even without incorporating an anti-CD3/CD28 polyclonal re-stimulation step at Day 12.

These results demonstrate that the culturing techniques provided herein perform well with cells from advanced cancer patients as well as healthy donors and that cultures can be pulsed with a cocktail of polypeptides, rather than a single polypeptide, to develop subsets of T-cells recognizing each of the polypeptides in the cocktail. These results also demonstrate that scaling up with Wilson-Wolf culture vessels is effective for expanding antigen-specific T-cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for producing a cell population comprising T cells having specificity for an antigen of interest, wherein said method comprises:
   (a) culturing a first cell population comprising PBMCs in the presence of GM-CSF for a first period of time to form a GM-CSF treated cell population,
   (b) culturing said GM-CSF treated cell population in the presence of resiquimod, *E. coli* lipopolysaccharide, and said antigen of interest for a second period of time to form an antigen treated cell population, and
   (c) culturing said antigen treated cell population in the presence of IL-7 for a third period of time to form said cell population comprising said T cells.

2. The method of claim 1, wherein the cells of said first cell population are human cells.

3. The method of claim 1, wherein said antigen of interest is a cancer-associated antigen.

4. The method of claim 3, wherein said cancer-associated antigen is MUC1, HER2/neu, mesothelin, WT1, NYEso-1, MART1, gp100, or TRP, or tumor cells processed by freeze/thawing, irradiation, homogenization, or heat killing.

5. The method of claim 1, wherein said antigen of interest is a pathogen-associated antigen.

6. The method of claim 5, wherein said pathogen-associated antigen is a cytomegalovirus, Epstein-Barr virus, human papilloma virus, *Mycobacterium tuberculosis, Candida albicans*, aspergillis, *Mycobacterium* avian *intracellularis*, Ebola virus, or HIV antigen.

7. The method of claim 1, wherein said first period of time is 18 to 24 hours.

8. The method of claim 1, wherein said second period of time is 16 to 30 hours.

9. The method of claim 1, wherein said third period of time is 10 to 22 days.

10. A method for providing a mammal with T cells having specificity for an antigen of interest, wherein said method comprises administering, to said mammal, a cell population produced by a method comprising:
    (a) culturing a first cell population comprising PBMCs in the presence of GM-CSF for a first period of time to form a GM-CSF treated cell population,
    (b) culturing said GM-CSF treated cell population in the presence of resiquimod, *E. coli* lipopolysaccharide, and said antigen of interest for a second period of time to form an antigen treated cell population, and
    (c) culturing said antigen treated cell population in the presence of IL-7 for a third period of time to form said cell population.

11. The method of claim 10, wherein said mammal is a human.

12. The method of claim 10, wherein the cells of said first cell population are human cells.

13. The method of claim 10, wherein said antigen of interest is a cancer-associated antigen.

14. The method of claim 13, wherein said cancer-associated antigen is MUC1, HER2/neu, mesothelin, WT1, NYEso-1, MART1, gp100, or TRP, or tumor cells processed by freeze/thawing, irradiation, homogenization, or heat killing.

15. The method of claim 10, wherein said antigen of interest is a pathogen-associated antigen.

16. The method of claim 15, wherein said pathogen-associated antigen is a cytomegalovirus, Epstein-Barr virus, human papilloma virus, *Mycobacterium tuberculosis, Candida albicans*, aspergillin, *Mycobacterium* avian *intracellularis*, Ebola virus, or HIV antigen.

17. The method of claim 10, wherein said first period of time is 18 to 24 hours.

18. The method of claim 10, wherein said second period of time is 16 to 30 hours.

19. The method of claim 10, wherein said third period of time is 10 to 22 days.

* * * * *